United States Patent
Knoepfle

(10) Patent No.: US 11,576,707 B2
(45) Date of Patent: Feb. 14, 2023

(54) FIXATION ASSEMBLY WITH A FLEXIBLE ELONGATED MEMBER FOR SECURING PARTS OF A STERNUM

(71) Applicant: Stryker European Operations Holdings, LLC, Wilmington, DE (US)

(72) Inventor: Christian Knoepfle, Donaueschingen (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 263 days.

(21) Appl. No.: 16/571,826

(22) Filed: Sep. 16, 2019

(65) Prior Publication Data

US 2020/0008849 A1    Jan. 9, 2020

Related U.S. Application Data

(63) Continuation of application No. 14/895,163, filed as application No. PCT/EP2013/066408 on Aug. 5, 2013, now Pat. No. 10,433,889.

(60) Provisional application No. 61/845,024, filed on Jul. 11, 2013.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/80* | (2006.01) |
| *A61B 17/00* | (2006.01) |
| *A61B 17/06* | (2006.01) |

(52) U.S. Cl.
CPC ........ *A61B 17/823* (2013.01); *A61B 17/8057* (2013.01); *A61B 17/8076* (2013.01); *A61B 2017/00004* (2013.01); *A61B 2017/06176* (2013.01)

(58) Field of Classification Search
CPC combination set(s) only.
See application file for complete search history.

(56) References Cited

U.S. PATENT DOCUMENTS

| | | | |
|---|---|---|---|
| 1,616,232 | A | 2/1927 | Roberts et al. |
| 3,469,573 | A | 9/1969 | Florio |
| 3,887,965 | A | 6/1975 | Schuplin |
| (Continued) | | | |

FOREIGN PATENT DOCUMENTS

| | | |
|---|---|---|
| CA | 2286111 A1 | 10/1998 |
| CA | 2439094 A1 | 9/2002 |
| (Continued) | | |

OTHER PUBLICATIONS

European Search Report for EP 13003896.1 dated Jul. 17, 2014.
(Continued)

*Primary Examiner* — Sameh R Boles
(74) *Attorney, Agent, or Firm* — Lerner, David, Littenberg, Krumholz & Mentlik, LLP

(57) ABSTRACT

A fixation assembly for securing parts of a sternum is provided. The assembly comprises a flexible elongated member and an attachment member. The flexible elongated member includes a locking structure configured to secure the flexible elongated member in a loop around the sternum parts. The attachment member has at least one opening for receiving a bone fastener and is coupled to the flexible elongated member.

20 Claims, 13 Drawing Sheets

(56) References Cited

U.S. PATENT DOCUMENTS

| | | | |
|---|---|---|---|
| 3,926,193 A | 12/1975 | Hasson | |
| 3,991,444 A | 11/1976 | Bailey | |
| 4,003,106 A | 1/1977 | Schumacher et al. | |
| 4,119,091 A | 10/1978 | Partridge | |
| 4,135,749 A | 1/1979 | Caveney et al. | |
| 4,136,148 A | 1/1979 | Joyce | |
| 4,201,215 A | 5/1980 | Crossett et al. | |
| 4,279,248 A | 7/1981 | Gabbay | |
| 4,473,524 A | 9/1984 | Paradis | |
| 4,512,346 A | 4/1985 | Lemole | |
| 4,535,764 A | 8/1985 | Ebert | |
| 4,583,541 A | 4/1986 | Barry | |
| 4,802,477 A | 2/1989 | Gabbay | |
| 4,874,370 A | 10/1989 | Heimerl et al. | |
| 4,944,753 A | 7/1990 | Burgess et al. | |
| 5,047,034 A | 9/1991 | Sohngen | |
| 5,139,498 A | 8/1992 | Astudillo Ley | |
| 5,146,654 A | 9/1992 | Caveney et al. | |
| 5,417,698 A | 5/1995 | Green et al. | |
| 5,549,619 A | 8/1996 | Peters et al. | |
| 5,653,711 A | 8/1997 | Hayano et al. | |
| 5,827,286 A | 10/1998 | Incavo et al. | |
| 5,941,881 A | 8/1999 | Barnes | |
| 5,964,763 A | 10/1999 | Incavo et al. | |
| 5,964,932 A | 10/1999 | Ison et al. | |
| 5,968,253 A | 10/1999 | Poser et al. | |
| 6,007,538 A | 12/1999 | Levin | |
| 6,051,007 A | 4/2000 | Hogendijk et al. | |
| 6,053,970 A | 4/2000 | Ison et al. | |
| 6,093,201 A | 7/2000 | Cooper et al. | |
| 6,200,318 B1 | 3/2001 | Har-Shai et al. | |
| 6,217,580 B1 | 4/2001 | Levin | |
| 6,302,899 B1 | 10/2001 | Johnson et al. | |
| 6,540,769 B1 | 4/2003 | Miller, III | |
| 6,872,210 B2 | 3/2005 | Hearn | |
| 6,969,398 B2 | 11/2005 | Stevens et al. | |
| 7,017,237 B2 | 3/2006 | Magno, Jr. et al. | |
| 7,033,377 B2 | 4/2006 | Miller, III | |
| 7,635,364 B2 | 12/2009 | Barrall et al. | |
| 7,695,473 B2 | 4/2010 | Ralph et al. | |
| 7,730,592 B2 | 6/2010 | Krisel | |
| 7,740,649 B2 | 6/2010 | Mosca et al. | |
| 7,871,411 B2 | 1/2011 | Grevious | |
| 7,934,297 B2 | 5/2011 | Williams | |
| 8,221,421 B2 | 7/2012 | Hearn | |
| 3,460,295 A1 | 6/2013 | McClellan et al. | |
| 8,460,295 B2 | 6/2013 | McClellan et al. | |
| 8,486,114 B2 | 7/2013 | Gillard et al. | |
| 9,358,054 B2 | 6/2016 | Garcia et al. | |
| 9,474,553 B2 | 10/2016 | Koch | |
| 10,292,742 B2 | 5/2019 | Knoepfle et al. | |
| 10,433,889 B2 | 10/2019 | Knoepfle | |
| 11,259,853 B2 | 3/2022 | Knoepfle | |
| 2002/0077659 A1 | 6/2002 | Johnson et al. | |
| 2002/0128654 A1 | 9/2002 | Steger et al. | |
| 2002/0143336 A1 | 10/2002 | Hearn | |
| 2003/0049324 A1 | 3/2003 | Vogt et al. | |
| 2003/0077381 A1 | 4/2003 | Scott et al. | |
| 2003/0083694 A1 | 5/2003 | Miller | |
| 2003/0212399 A1 | 11/2003 | Dinh et al. | |
| 2004/0010256 A1 | 1/2004 | Gabbay | |
| 2004/0133206 A1 | 7/2004 | Stevens et al. | |
| 2005/0070928 A1 | 3/2005 | Heino et al. | |
| 2005/0124996 A1 | 6/2005 | Hearn | |
| 2005/0267475 A1 | 12/2005 | Miller | |
| 2005/0288674 A1 | 12/2005 | Golobek | |
| 2006/0116683 A1 | 6/2006 | Barrall et al. | |
| 2006/0122611 A1 | 6/2006 | Morales et al. | |
| 2006/0134160 A1 | 6/2006 | Troczynski et al. | |
| 2006/0161161 A1 | 7/2006 | Shifrin et al. | |
| 2006/0195101 A1 | 8/2006 | Stevens | |
| 2006/0259141 A1 | 11/2006 | Roman et al. | |
| 2006/0276794 A1 | 12/2006 | Stern | |
| 2007/0038218 A1 | 2/2007 | Grevious | |
| 2007/0043371 A1 | 2/2007 | Teague et al. | |
| 2007/0213832 A1 | 9/2007 | Wen | |
| 2007/0259101 A1 | 11/2007 | Kleiner et al. | |
| 2008/0154312 A1 | 6/2008 | Colleran et al. | |
| 2008/0221578 A1 | 9/2008 | Zeitani | |
| 2008/0306579 A1 | 12/2008 | Dolan et al. | |
| 2009/0118774 A1 | 5/2009 | Miller, III | |
| 2009/0118775 A1 | 5/2009 | Burke | |
| 2009/0138054 A1 | 5/2009 | Teague et al. | |
| 2009/0234357 A1 | 9/2009 | Morales et al. | |
| 2009/0234358 A1 | 9/2009 | Morales et al. | |
| 2009/0248091 A1 | 10/2009 | Teague et al. | |
| 2009/0269480 A1 | 10/2009 | Berglund | |
| 2010/0094294 A1 | 4/2010 | Gillard et al. | |
| 2010/0179600 A1 | 7/2010 | Steger et al. | |
| 2010/0305569 A1 | 12/2010 | Leuenberger et al. | |
| 2010/0318085 A1 | 12/2010 | Austin et al. | |
| 2011/0015681 A1 | 1/2011 | Elsbury | |
| 2011/0125193 A1 | 5/2011 | Grevious | |
| 2011/0166612 A1 | 7/2011 | Bardaji Pascual et al. | |
| 2011/0295257 A1* | 12/2011 | McClellan | A61B 17/823 606/74 |
| 2011/0313474 A1 | 12/2011 | Gabele | |
| 2013/0261625 A1 | 10/2013 | Koch et al. | |
| 2013/0338719 A1 | 12/2013 | Madjarov | |
| 2014/0100573 A1 | 4/2014 | Llas Vargas et al. | |
| 2014/0142638 A1 | 5/2014 | Goodwin et al. | |
| 2015/0045794 A1 | 2/2015 | Garcia et al. | |

FOREIGN PATENT DOCUMENTS

| | | |
|---|---|---|
| CN | 101537208 A | 9/2009 |
| CN | 202235628 U | 5/2012 |
| DE | 202004021763 U1 | 9/2010 |
| DE | 102010021737 A1 | 11/2011 |
| DE | 102011109677 A1 | 2/2013 |
| EP | 0238219 A1 | 9/1987 |
| EP | 0597259 A2 | 5/1994 |
| EP | 0608592 A1 | 8/1994 |
| EP | 0806212 A1 | 11/1997 |
| EP | 0608592 B1 | 8/1998 |
| EP | 1099416 A2 | 5/2001 |
| EP | 1121058 A1 | 8/2001 |
| EP | 1521552 A1 | 4/2005 |
| EP | 1365693 B1 | 1/2006 |
| EP | 1429674 B1 | 3/2006 |
| EP | 1654994 A1 | 5/2006 |
| EP | 1691702 A1 | 8/2006 |
| EP | 1732460 B1 | 5/2010 |
| EP | 1885268 B1 | 7/2010 |
| EP | 2063799 B1 | 9/2010 |
| EP | 2367489 A1 | 9/2011 |
| EP | 1748738 B1 | 10/2011 |
| EP | 3042622 A1 | 7/2016 |
| WO | 9004366 A1 | 5/1990 |
| WO | 9505782 A1 | 3/1995 |
| WO | 9844850 A1 | 10/1998 |
| WO | 0022992 A1 | 4/2000 |
| WO | 02/067795 A1 | 9/2002 |
| WO | 03037201 A1 | 5/2003 |
| WO | 2004006784 A1 | 1/2004 |
| WO | 2004078218 A2 | 9/2004 |
| WO | 2005055844 A1 | 6/2005 |
| WO | 2005117726 A2 | 12/2005 |
| WO | 2006135935 A1 | 12/2006 |
| WO | 2007084238 A2 | 7/2007 |
| WO | 2008034537 A1 | 3/2008 |
| WO | 2009100792 A2 | 8/2009 |
| WO | 2010042946 A1 | 3/2010 |
| WO | 2010042946 A1 | 4/2010 |
| WO | 2010126436 A1 | 11/2010 |
| WO | 2011153676 A1 | 12/2011 |
| WO | 2013013218 A2 | 1/2013 |
| WO | 2013067049 A1 | 5/2013 |
| WO | 2013072576 A1 | 5/2013 |
| WO | 2014081574 A1 | 5/2014 |

(56) References Cited

FOREIGN PATENT DOCUMENTS

WO  2014144479 A1  9/2014
WO  2015142588 A2  9/2015

OTHER PUBLICATIONS

Extended European Search Report for Application No. 15000033.9 dated Jun. 24, 2015.
Hutson et al, Infections in Periarticular Fractures of the Lower Extremity Treated with Tensioned Wire Hybrid Fixators, Journal of Orthopaedic Trauma vol. 12, No. 3, 1998, pp. 214-218.
International Preliminary Report on Patentability Chapter II, for Application No. PCT/EP2013/066408 dated Sep. 25, 2015.
International Search Report and Written Opinion for Application No. PCT/EP2013/066408 dated Oct. 22, 2013.
Synthes CMF, "Modular Sternal Cable System", 2006, 12 pages.
Synthes CMF, "Sternal ZipFix System—For fast and stable fixation of the sternum", Technique Guide, 2011, 26 pages.
European Search Report for Application No. EP16002390.9 dated Mar. 31, 2017.

* cited by examiner

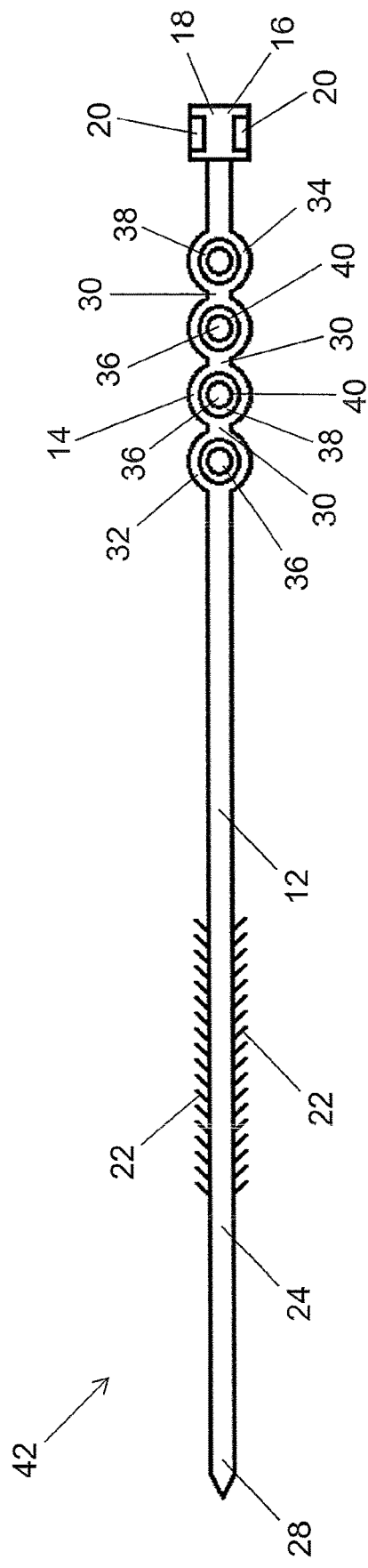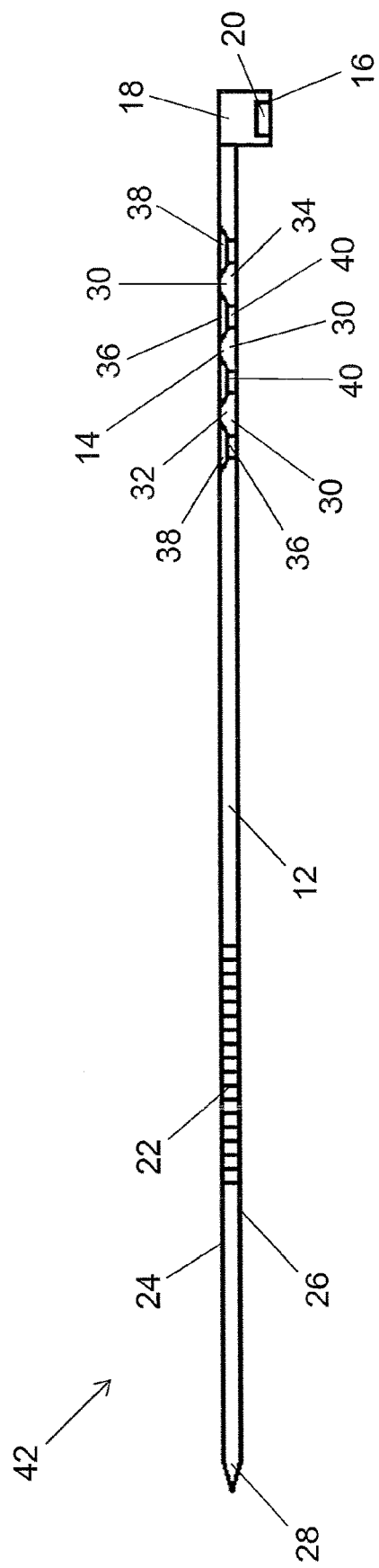
Fig. 2a
Fig. 2b

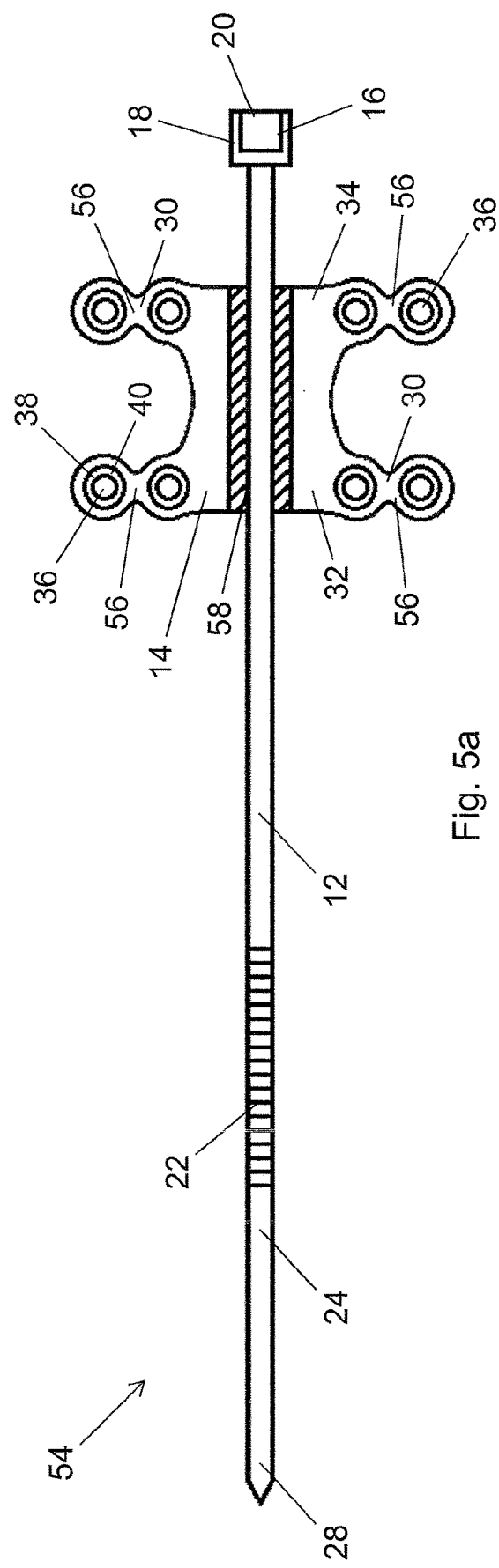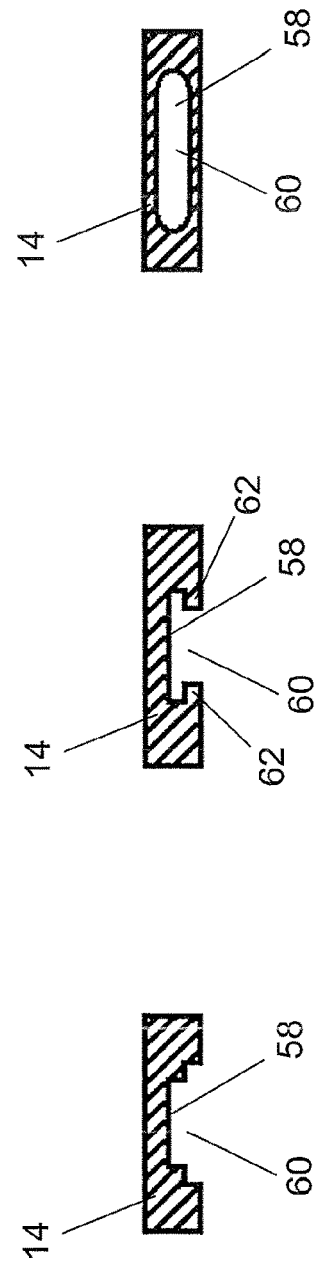

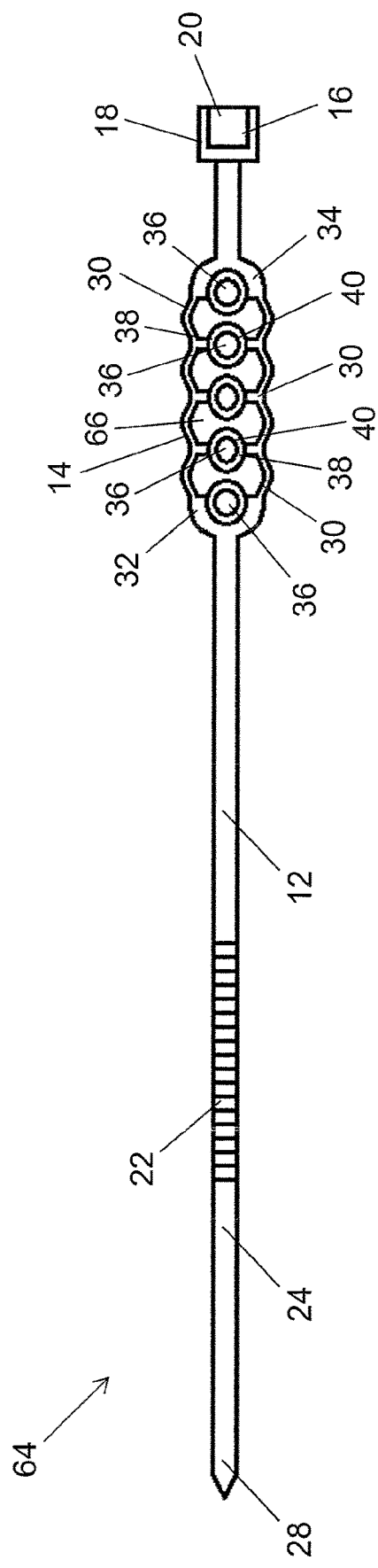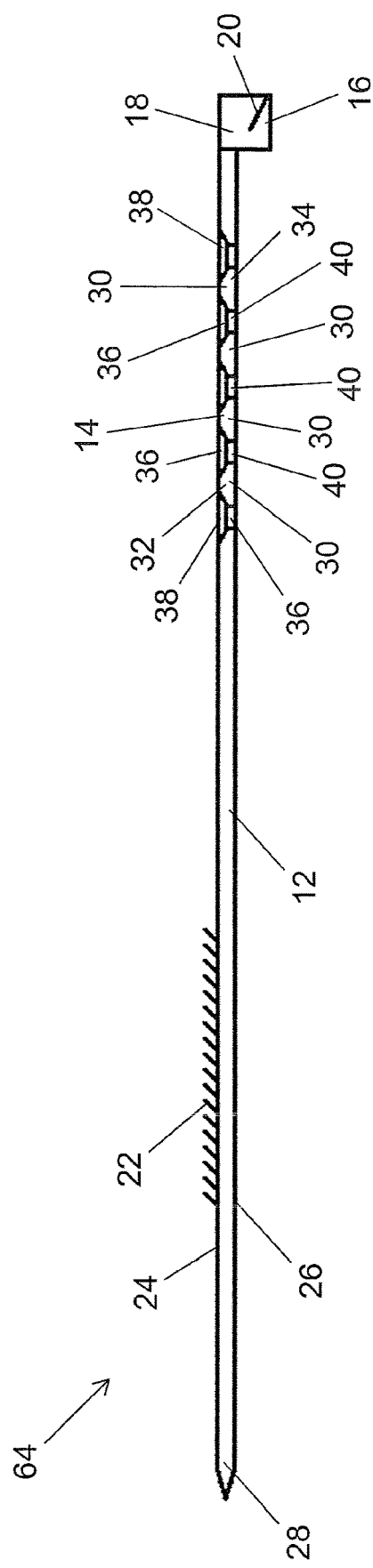
Fig. 6a
Fig. 6b

FIXATION ASSEMBLY WITH A FLEXIBLE ELONGATED MEMBER FOR SECURING PARTS OF A STERNUM

CROSS-REFERENCE TO RELATED APPLICATIONS

This application is a continuation of U.S. patent application Ser. No. 14/895,163, filed on Dec. 1, 2015, which is a national phase entry under 35 U.S.C. § 371 of International Application No. PCT/EP2013/066408 filed Aug. 5, 2013, published in English, which claims priority from U.S. Provisional Patent Application No. 61/845,024 filed Jul. 11, 2013, all of which are incorporated herein by reference.

TECHNICAL FIELD

The present disclosure generally relates to sternal fixation. Specifically, the disclosure relates to a fixation assembly for securing parts of a sternum and to a system compromising the fixation assembly.

BACKGROUND OF THE INVENTION

Various surgical procedures require the surgeon to access the thoracic region of a patient. A known procedure to access the thoracic region is to cut the sternum in two parts and separate these two parts from each other. After completion of the surgical procedure, the separated parts of the sternum are brought back to their initial position and fixed, for example, with a bone plate attached to the sternum parts or a wire tensioned around the circumference of the sternum.

EP 0 597 259 A2 discloses a wound closure element to be looped around a human sternum. The wound closure element comprises a strap which is inserted through and retained by a tightening plate.

U.S. Pat. No. 8,460,295 B2 discloses a sternum repair device including a central body and plurality of bands extending from the central body. The bands may wrap around the sternum to keep the separate sternum parts together. The central body includes a view window which is used by a surgeon to line up the device during installation on the sternum.

WO 2010/042946 A1 discloses a cerclage system including a cable that encircles the sternum parts and a bone plate having channels to receive segments of the cable. The bone plate further includes a pair of locking studs to lock the cable within the channels to the bone plate.

EP 0 608 592 B1 discloses an assembly for banding a sternum. The assembly comprises an elongated flexible band, a needle at one end of the band and a buckle proximate the other end of the band. A main section of the band includes a plurality of spaced slots which can engage at a locking mechanism.

After a surgical procedure such as, for example, a bypass operation has been carried out on a patient and the sternum has been closed using any of the known fixation assemblies, the patient is normally kept under surveillance. If it is detected that the surgical procedure has failed in any manner, it may be desirable for the surgeon to again open the sternum closure. The time required for this sternum opening procedure may be critical for the patient's health and even life. Moreover, a cable or wire tensioned around the sternum parts (so-called "primary closure") might come loose or brake due to the load applied to the thoracic region of the patient. In such a case, the fixation has to be stabilized by, for example, a bone plate (so-called "secondary closure")

BRIEF SUMMARY OF THE INVENTION

There is a need for a fixation assembly for securing parts of a sternum that can be attached or separated fast, easily and at low risk for the patient. Furthermore, there is a need for a fixation assembly which provides a high assembly-sternum-construct-stability. Moreover, there is a need for a fixation assembly for securing parts of a sternum that exhibits good surgical results.

Further aspects of the present disclosure are directed to the provision of a fixation assembly and fixation systems that facilitate a rapid healing of a sternum and guarantee a stable configuration of both the fixation system and the sternum parts.

According to one aspect, there is provided a fixation assembly for securing parts of a sternum. The fixation assembly comprises a flexible elongated member and an attachment member. The flexible elongated member includes a locking structure configured to secure the flexible elongated member in a loop around the sternum parts. The attachment member has at least one opening for receiving a bone fastener and the attachment member is coupled to the flexible elongated member.

The attachment member may be formed as an insert in the flexible elongated member. In one realization, the attachment member can be cast in the flexible elongated member. Alternatively, or in addition, the flexible elongated member may have a receiving structure configured to receive the attachment member. The attachment member can be held in the receiving structure by a form fit. For example, the form fit may be realized by a snap fit. The receiving structure may be configured to establish the holding of the attachment member by a snap fit. This may be accomplished with a flexible or elastic protrusion of the receiving structure.

Further, the receiving structure may include at least one opening. The at least one opening of the receiving structure may substantially overlap with the at least one opening of the attachment member. At least a part of the receiving structure may have a thickness which is larger than or substantially equal to a thickness of the flexible elongated member.

In one implementation, the attachment member may include a guiding structure for slideably engaging the flexible elongated member. The guiding structure of the attachment member may be formed as a recess or an opening. The recess or the opening may slideably receive the flexible elongated member. The recess or the opening may have a shape adapted to guide the flexible elongated member in at least one direction.

The attachment member may be adapted to be slided onto the flexible elongated member. Alternatively, or in addition, the attachment member may be adapted to be clamped on the flexible elongated member.

In one realization, the at least one opening of the attachment member may include a locking feature configured to lock a bone fastener to the attachment member. The locking feature may include a threaded portion or one or more lips in a circumferential direction adapted to engage a bone fastener (e.g., a threaded head thereof). Further, the locking feature may engage a threaded head of a bone fastener at a selected angular orientation. The at least one opening of the attachment member may have a multiple thread (e.g., a double thread). Further, the at least one opening of the attachment member may comprise a threaded portion on a bone contacting side of the attachment member and an unthreaded portion on a side opposite to the bone contacting side.

The at least one opening of the attachment member may have a conical, convex or spherical taper which substantially tapers inwardly in a direction toward a bone contacting surface of the attachment member. Thus, at least one opening of the attachment member can be configured to exert a force on the attachment member when a bone fastener is screwed or inserted through the opening into the sternum.

In one implementation, the at least one opening of the attachment member may have an inclined surface onto which a bone fastener is able to slide in a fastening or compression position. The at least one opening of the attachment member may permit a bone fastener to slide laterally or longitudinally with respect to the opening or the attachment member. Further, at least one opening of the attachment member may define a predetermined direction for a bone fastener. The inclined surface may have a predetermined angle with respect to an extension plane of the attachment member. The predetermined angle can be between about 20 and 70 degrees, for example about 40 to 50 degrees (e.g., about 45 degrees).

The at least one opening of the attachment member may be a circular or elongated hole. The elongated hole may be an oblong hole. Further, the elongated hole may extend substantially parallel with respect to a longitudinal direction of the attachment member or of the flexible elongated member. Alternatively, the elongated hole may extend substantially perpendicular to a longitudinal direction of the attachment member or of the flexible elongated member.

The opening may have a width in a direction perpendicular to an extension of the flexible elongated member that substantially corresponds to a width of the flexible elongated member at a distance from the opening. In other words, the fixation assembly may have a larger width in a region of the one or more openings compared to a width of the flexible elongated member along most of its extension. In a similar manner, the thickness of the fixation assembly may be larger in a region of the one or more openings compared to a thickness of the flexible elongated member at a distance therefrom.

The attachment member may include multiple openings for receiving bone fasteners. The attachment member may have an opening for receiving a bone fastener substantially perpendicular to bone. In one implementation, the attachment member may include a hole for receiving a bone fastener substantially perpendicular to bone and arranged substantially aligned with an oblong hole along a longitudinal direction of the attachment member or, alternatively, along a line substantially perpendicular to a longitudinal direction of the attachment member. Alternatively, or in addition, a hole having a locking feature for engaging a threaded head of a bone fastener at a selected angular orientation may be arranged on the attachment member substantially aligned with an elongated hole along a longitudinal direction of the attachment member or along a line which is substantially perpendicular to a longitudinal direction of the attachment member.

The attachment member may comprise an alternate arrangement of holes (locking holes) having a locking feature for locking a bone fastener to the attachment member and elongated (or oblong) holes. For example, the first and third holes of a first section of the attachment member and the second and fourth holes of a second section of the attachment member may be elongated holes and/or the second and fourth holes of the first section of the attachment member and the first and the second holes of the second section of the attachment member may be holes having a locking feature for locking a bone fastener to the attachment member. Alternatively, or in addition, the locking holes may receive a bone fastener substantially perpendicular to bone.

The at least one opening of the attachment member may have a central axis which is oblique relative a vertical axis of the attachment member, e.g. of an extension plane thereof. An angle defined between the central axis and the vertical axis can be approximately between 0° and 60°. Alternatively, the at least one opening of the attachment member may be oblique relative to an upper surface (e.g., a side opposite a bone contacting side) or lower surface (e.g., a bone contacting side) of the attachment member.

In one realization, the attachment member may be configured to be cut with a surgical tool. The attachment member may define at least one cutting line or cutting edge. Thus, the attachment member can be adapted in its shape and dimensions. Further, the number of openings of the attachment member can be adapted by cutting or trimming the attachment member. The surgical tool may be a cutting device, e.g., a plier or surgical scissor.

In one implementation, each of the flexible elongated member and the attachment member may define a width in a transverse direction thereof. The width of the attachment member may be larger than a substantially equal to the width of the flexible elongated member. Each of the flexible elongated member and the attachment member may have a thickness. The thickness of the attachment member may be larger than a substantially equal to the thickness of a flexible elongated member.

A longitudinal orientation (or longitudinal direction) of the attachment member can be substantial along a longitudinal direction of the flexible elongated member or can be substantially perpendicular thereto. The attachment member may have an undulating outer contour. Thus, an outer peripheral surface of the attachment member may have an undulating shape, such that the attachment member can have a waisted shape. Alternatively, or in addition, the attachment member may have a straight outer contour. Further, in one realization, the attachment member may have at least one extension element or arm extending from a central body of the attachment member. For example, the attachment member may have two, three or four arms extending therefrom.

In one implementation, the locking structure of the flexible elongated member may be arranged at or near one end of the flexible elongated member. The locking structure of the flexible elongated member may include a latching mechanism configured to lock the flexible elongated member in a loop configuration.

Further, the flexible elongated member can include teeth, barbs or claws arranged along a longitudinal direction of the flexible elongated member and lockable with the latching mechanism. The teeth, barbs or claws may be arranged on a side opposite a bone contacting side of the flexible elongated member. Alternatively, or in addition, the teeth, barbs or claws can be arranged on one or more lateral surfaces of the flexible elongated member.

Alternatively or, in addition, the flexible elongated member may include at least one opening or slot which is configured to engage at the locking structure of the flexible elongated member (i.e., which are lockable with the latching mechanism). Thus, the flexible elongated member may include at least one opening or slot which is lockable with the latching mechanism. The flexible elongated member may include a plurality of such openings or slots. The openings or slots may be arranged along a longitudinal direction of the flexible elongated member. The openings or slots may be arranged at a main (middle) portion or an end portion of the flexible elongated member. In one implementation, the openings or slots can be arranged at an end portion opposite or proximate the end having the locking structure of the flexible elongated member.

The latching mechanism can include at least one pawl, serration or lip, which is configured to engage the teeth, barbs or claws of the flexible elongated member such that, once snapped in place, the corresponding tooth, barb claw will not be able to back out. Alternatively or, in addition, the latching mechanism may include at least one pawl, serration or lip which is configured to engage on the at least one opening or slot of the flexible elongated member such that, once snapped in place, the corresponding opening or slot will not be able to back out.

Further, the latching mechanism may include a through opening configured to receive a part of the flexible elongated member. An inner surface of the through opening of the latching mechanism can include the at least one pawl, serration or lip.

In one realization, the flexible elongated member may include a needle or a hook at an end thereof. The needle or hook may substantially be rigid (e.g., in comparison to the flexible elongated member). The locking structure of the flexible elongated member can be arranged at an end of the flexible elongated member opposite to the end at which the needle or hook is arranged. The needle or hook may therefore be arranged at one end of the flexible elongated member and the locking structure may be arranged proximate at the other end of the flexible elongated member. Furthermore, the end of the flexible elongated member including a needle or hook is configured to be inserted through the through opening of the latching mechanism.

The needle or hook may define a width in a transverse direction thereof. The width of the needle or hook may be smaller than a width of the flexible elongated member. Alternatively, the width of the needle or hook can be substantially equal to the width of the flexible elongated member. Further, the needle or hook may have a thickness. The thickness of the needle or hook may be smaller than a thickness of the flexible elongated member. Alternatively, the thickness of the needle or hook can be substantially equal to the thickness of the flexible elongated member. The needle or hook may have a pointed end, a sharp end, a tip end or a blunt end.

The flexible elongated member may have a predetermined breaking line or perforation or, alternatively, a predetermined cutting line or perforation. The breaking or cutting line/perforation may be arranged near one end of the flexible elongated member. Thus, the breaking or cutting line/perforation may be arranged near the needle or hook shaped end of the flexible elongated member.

The flexible elongated member and the attachment member may be integrally formed. In other words, the flexible elongated member and the attachment member may be formed from one piece. Alternatively, the flexible elongated member and the attachment member can be separate parts from each other.

The flexible elongated member can be made from at least one of titanium, an alloy of titanium, stainless steel, polyetheretherketone (PEEK) and a resorbable material. Further, the attachment member may be made from at least one of titanium, an alloy of titanium, stainless steel, polyetheretherketone (PEEK) and a resorbable material.

The flexible elongated member or the attachment member can be made from a biocompatible material, for example, a biocompatible metal.

The flexible elongated member may be a band, cable, wire or cerclage. Alternatively, the flexible elongated member can be a strap or a ribbon. In one implementation, the flexible elongated member can be formed as a zip tie.

The attachment member can be formed as a bone plate. Alternatively, the attachment member can be formed as a mash.

At least a part of the flexible elongated member or at least a part of the attachment member can be pre-formed. Thus, the flexible elongated member or the attachment member may have a shape that substantially conforms with the sternum. Alternatively, or in addition, at least a part of the flexible elongated member or at least a part of the attachment member may be pre-bent flexible. This flexibility may allow the fixation assembly to flex about an axis in its extension plane. Alternatively, or in addition, a surface (e.g., a lower surface) of the flexible elongated member or of the attachment member may have a profile that substantially conforms with the sternum. This profile may have a concave appearance or shape. Furthermore, this profile or pre-forming may be made generic or patient specific, for example by adapting the shape of the profile or the pre-form based on a computed tomographic (CT) scan of the sternum of a patient.

In one realization, the attachment member may include at least one bridge configured to be cut with a surgical tool. The surgical tool may be a cutting device, a plier or surgical scissor.

The attachment member may include a first section configured to be secured to the sternum and a second section configured to be secured to the sternum. Thus, the first section of the attachment member can be secured to a first sternum part and the second section of the attachment member can be secured to a second sternum part. Each of the first section and the second section may have at least one opening for receiving a bone fastener. The at least one opening can be configured as generally described above or hereinafter.

The at least one bridge may be configured to connect the first and second section of the attachment member to each other. In one implementation, the attachment member may include multiple bridges. At least two bridges can be arranged parallel to each other.

According to a further aspect, there is provided a fixation system for securing parts of a sternum, comprising a fixation assembly as generally described above and hereinafter and at least one bone fastener. The at least one bone fastener may be a locking screw, a cortical screw, a compression screw or a bone peg. The at least one bone fastener may be a bone screw with a threaded head for (e.g., monoaxial or polyaxial) engagement of the locking feature of the at least one opening of the attachment member at a desired angle. The system may further comprise a surgical tool for cutting the attachment member or the at least one bridge of the attachment member.

According to a further aspect, there is provided a fixation system for securing parts of a sternum, comprising a fixation assembly as generally described above and hereinafter and a further attachment member.

In the above aspect, the further attachment member can be formed as a bone plate. Alternatively, the further attachment member can be formed as a mesh.

The further attachment member may be configured and defined as the attachment member of the fixation assembly as generally described above and hereinafter.

The further attachment member can be made from at least one of titanium, an alloy of titanium, stainless steel, polyetheretherketone (PEEK) and a resorbable material.

Moreover, the further attachment member may include at least one opening for receiving a bone fastener. The at least one opening of the further attachment member can include a locking feature configured to lock a bone fastener to the further attachment member. The locking feature can include a threaded portion or one or more lips in a circumferential direction adapted to engage a bone fastener (e.g., a threaded head thereof). Further, the locking feature may engage a threaded head of a bone fastener at a selected angular orientation. The at least one opening of the further attachment member may have a multiple thread (e.g., a double thread). Moreover, the at least one opening of the further attachment member may comprise a threaded portion on a bone facing side of the further attachment member and an unthreaded portion on a side opposite to the bone facing side.

In one implementation, the at least one opening of the further attachment member may have a conical, convex or spherical taper which substantially tapers inwardly in a direction toward a bone facing surface of the further attachment member.

The at least one opening of the further attachment member can be a circular or elongated hole. In one realization, the further attachment member may include multiple openings for receiving bone fasteners.

Moreover, the at least one opening of the further attachment member may have an inclined surface onto which a bone fastener is able to slide in a fastening or compression position. The at least one opening of the further attachment member may permit a bone fastener to slide laterally or longitudinally with respect to the opening or the further attachment member. Moreover, at least one opening of the further attachment member may define a predetermined direction for a bone fastener. The inclined surface may have a predetermined angle with respect to an extension plane of the further attachment member. The predetermined angle can be between about 20 and 70 degrees, for example about 40 to 50 degrees (e.g., about 45 degrees).

The at least one opening of the further attachment member may have a central axis which is oblique relative a vertical axis of the further attachment member, e.g. of an extension plane thereof. An angle defined between the central axis and the vertical axis can be approximately between 0° and 60°. Alternatively, the at least one opening of the further attachment member may be oblique relative to an upper surface (e.g., a side opposite a bone facing side) or lower surface (e.g., a bone facing side) of the further attachment member.

The further attachment member may be configured to be cut with a surgical tool, e.g., with a cutting device, a plier or surgical scissor.

In one implementation, the further attachment member may include a receiving structure configured to receive at least a part of the fixation assembly (e.g., a part of the flexible elongated member or a part of the attachment member). The receiving structure of the further attachment member can be arranged on a bone facing side of the further attachment member. Moreover, the receiving structure of the further attachment member may be a recess, an opening or a groove. The receiving structure may extend substantially along a longitudinal axis of the further attachment member or substantially perpendicular thereto. Thus, the receiving structure may extend substantially in a direction of a longitudinal axis of the flexible elongated member. Further, the receiving structure of the further attachment member may be arranged at a central portion of the further attachment member. The receiving structure of the further attachment member may be configured to receive a surgical wire (e.g., a Kirschner wire, K-wire).

Alternatively, or in addition, the further attachment member may include at least one recess configured to receive a surgical wire, such as a Kirschner wire (K-wire). The at least one recess can be arranged on a bone facing side of the further attachment member. Moreover, the at least one recess may be formed as an opening or a groove. The recess can be substantially O-, U- or V-shaped in cross-section. The at least one recess for receiving a surgical wire may extend substantially along a longitudinal axis of the further attachment member or substantially perpendicular thereto. Thus, the recess may extend substantially in a direction of a longitudinal axis of the flexible elongated member. Further, the at least one recess for receiving a surgical wire may be arranged at a central (middle) portion or at an outer portion (e.g. at an arm or section extending from the central portion) of the further attachment member.

The further attachment member may include at least one bridge configured to be cut with a surgical tool.

In one realization, the further attachment member can include a first section configured to be secured to the sternum, e.g., to a first sternum part, and a second section configured to be secured to the sternum, e.g., to a second sternum part. Each of the first section and the second section of the further attachment member may have at least one opening for receiving a bone fastener. The at least one opening of the first or second section may be configured and defined as the at least one opening of the attachment member of the fixation assembly as generally described and defined above and hereinafter. The at least one bridge of the further attachment member can be configured to connect the first and second section to each other.

In one realization, the further attachment member may include multiple bridges. At least two bridges can be arranged parallel to each other. In one implementation, the at least one bridge of the attachment member of the fixation assembly may substantially overlap with the at least one bridge of the further attachment member. Thus, the at least one bridge of the attachment member of the fixation assembly and the at least one bridge of the further attachment member can be cut with a surgical tool within one single cutting step.

In the aspect described above, the fixation system may further comprise at least one bone fastener. The at least one bone fastener may be configured to fasten the further attachment member to the fixation assembly and/or to bone. The at least one bone fastener may be a bone screw with a threaded head for (e.g., monoaxial or polyaxial) engagement of the locking feature of the at least one opening of the further attachment member and/or the locking feature of the at least one opening of the attachment member of the fixation assembly. Moreover, the at least one bone fastener may be a locking screw, a cortical screw, a compression screw or a bone peg. The system may further comprise a surgical tool for cutting the further attachment member or the at least one bridge of the further attachment member.

BRIEF DESCRIPTION OF THE DRAWINGS

The above and other features, aspects and advantages of the present disclosure will become apparent from the following detailed description taken in conjunction with the accompanying drawings wherein:

FIG. 1b is a cross-sectional view of the fixation assembly shown in FIG. 1a;

FIG. 2a is a top view of a fixation assembly according a second embodiment;

FIG. 2b is a cross-sectional view of the fixation assembly shown in FIG. 2a;

FIG. 3b is a cross-sectional view of the fixation assembly shown in FIG. 3a;

FIG. 4b is a cross-sectional view of the fixation assembly shown in FIG. 4a;

FIG. 5a is a top view of a fixation assembly according to a fifth embodiment;

FIG. 5b is a detailed cross-sectional view of the fixation assembly shown in FIG. 5a;

FIG. 5c is a detailed cross-sectional view of another embodiment of the fixation assembly shown in FIG. 5a;

FIG. 5d is a detailed cross-sectional view of another embodiment of the fixation assembly shown in FIG. 5a;

FIG. 6a is a top view of a fixation assembly according to a sixth embodiment;

FIG. 6b is a cross-sectional view of the fixation assembly shown in FIG. 6a;

DETAILED DESCRIPTION

Figure 1A:
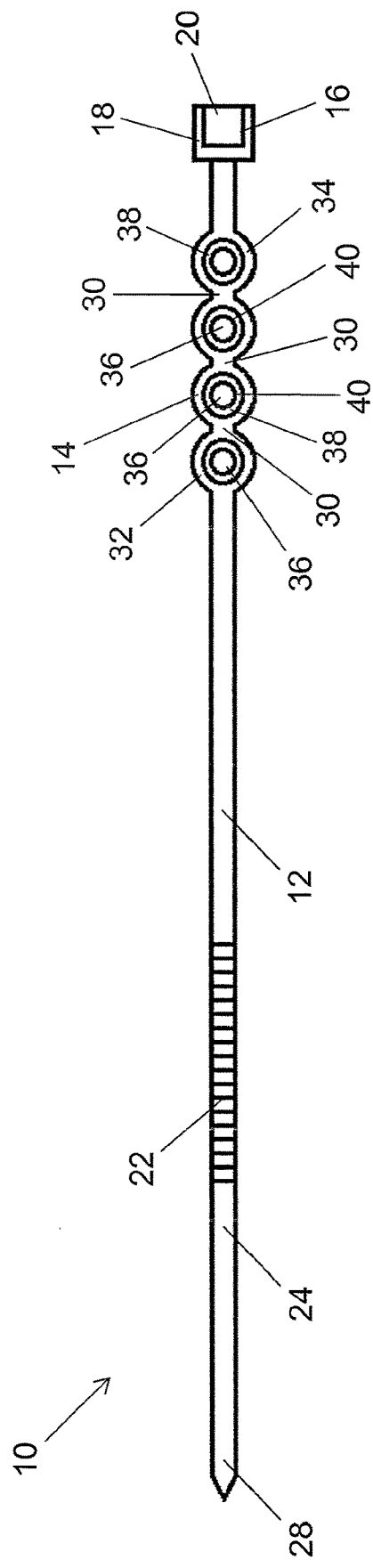
FIG. 1a is a top view of a fixation assembly according to a first embodiment.

In the following, embodiments of a fixation assembly and a fixation system for securing parts of a sternum will be described. The same reference numerals will be used to denote the same or similar structural features.

Referring to FIG. 1a, there is shown a top view of a first embodiment of a fixation assembly 10 for securing parts of a sternum. The fixation assembly 10 comprises a flexible elongated member 12 and an attachment member 14. The flexible elongated member 12 includes a locking structure 16 which is configured to secure the flexible elongated member 12 in a loop around the sternum parts. As shown in FIG. 1a, the attachment member 14 is coupled to the flexible elongated member 12. In the present embodiment, the flexible elongated member 12 and the attachment member 14 are integrally formed.

The flexible elongated member 12 is, as shown in FIG. 1a, a band, e.g., a strap or ribbon. Alternatively, the flexible elongated member 12 can be a cable, wire or cerclage. Further, the flexible elongated member 12 and the attachment member 14 are made from titanium. Alternatively, the flexible elongated member 12 and/or the attachment member 14 may be made from an alloy of titanium, stainless steel, polyetheretherketone (PEEK) or a resorbable material. In the present embodiment, the attachment member 14 is formed as a bone plate. At least a part of the flexible elongated member 12 or the attachment member 14 can be pre-formed (not shown in FIG. 1a).

As can be seen in FIG. 1a, the locking structure 16 of the flexible elongated member 12 is arranged near one end of the flexible elongated member 12. In the present embodiment, the locking structure 16 of the flexible elongated member 12 is arranged at an end (in FIG. 1a on the right side) of the flexible elongated member 12. The locking structure 16 includes a latching mechanism which is configured to lock the flexible elongated member 12 in a loop configuration, e.g., in a loop around sternum parts. The latching mechanism includes a through opening 18. The through opening 18 is configured to receive a part of the flexible elongated member 12. Further, the latching mechanism includes at least one, in the present embodiment a single one, pawl 20. Alternatively, the latching mechanism includes at least one serration or lip. As shown in FIG. 1a, an inner surface of the through opening 18 of the latching mechanism includes the pawl 20.

The flexible elongated member 12 further includes teeth 22. Alternatively, the flexible elongated member 12 includes barbs or claws. The teeth 22 of the flexible elongated member 12 are arranged along a longitudinal direction of the flexible elongated member 12 and are lockable with the latching mechanism. The teeth 22 are positioned on a side 24 opposite a bone contacting side 26 of the flexible elongated member 12. Thus, the teeth 22 of the flexible elongated member 12 do not interfere or infringe surrounding tissue or bone.

The other end of the flexible elongated member 12 (on the left side in FIG. 1a) can be inserted through the through opening 18 of the latching mechanism of the locking structure 17 which is arranged on the other, opposite end of the flexible elongated member 12. The pawl 20 of the latching mechanism is configured to engage the teeth 22 of the flexible elongated member 12. Thus, once the end of the flexible elongated member 12 opposite to the locking structure 16 is inserted through the through opening 18 of the latching mechanism and the teeth 22 are snapped in place by engaging on the pawl 20 of the locking structure 16, the corresponding tooth 22 will not be able to back out. Thus, in the present embodiment, the flexible elongated member 12 is formed as a zip tie.

As shown in FIG. 1a, the end of the flexible elongated member 12 which is insertable through the through opening 18 of the latching mechanism, e.g., the end of the flexible elongated member 12 opposite to the locking structure 16, includes a needle 28. Alternatively, the flexible elongated member 12 includes a hook at an end thereof. The needle shaped end 28 of the flexible elongated member 12 facilitates the implantation and insertion of the fixation assembly 10 on and around the sternum of a patient.

As can be seen in FIG. 1a, each of the flexible elongated members 12 and the attachment member 14 defines a width in a transverse direction thereof. The width of the attachment member 14 is, in the present embodiment, larger than the width of flexible elongated member 12. Alternatively, the width of the attachment member 14 can be substantially equal to the width of the flexible elongated member 12. Further, a longitudinal orientation of the attachment member 14 is substantially along a longitudinal direction of the flexible elongated member 12. As shown in FIG. 1a, the attachment member 14 has an undulating outer contour. In the present embodiment, an outer peripheral surface of the attachment member 14 has an undulating shape, such that the attachment member 14 has a waisted shape. Thus, the attachment member 14 includes at least one bridge 30 which is defined by the undulating outer contour. The attachment member 14 is configured to be cut with a surgical tool such as a plier or a cutting device. In the present embodiment, the attachment member 14 includes three bridges 30. Thus, the attachment member 14 includes multiple bridges 30. Each of the bridges 30 of the attachment member 14 is configured to be cut with a surgical tool. Further, each bridge 30 defines a cutting section or cutting line alone which a surgeon can cut the attachment member 14 with the surgical tool.

Further, the attachment member 14 includes a first section 32 configured to be secured to the sternum and a second section 34 configured to be secured to the sternum. The first section 32 can thus be secured to a first sternum part and the second section can be secured to a second sternum part, e.g., separated from the first sternum part. As shown in FIG. 1a, one bridge 30 connects the first and the second section 32, 34 to each other.

Further, at least two, in the present embodiment all, bridges 30 are arranged parallel to each other. As can be seen in FIG. 1a, the attachment member 14 has at least one opening 36 for receiving a bone fastener (not shown in FIG. 1a). In the present embodiment, the attachment member 14 includes four openings 36. The attachment member 14 thus includes multiple openings 36 for receiving bone fasteners. These openings 36 are arranged substantially along a longitudinal direction of the attachment member 14. As shown in FIG. 1a, each of the first section 32 and the second section 34 has at least one opening 36 for receiving a bone fastener. In the present embodiment, the first section 32 includes two openings 36 and the second section 34 includes also two openings 36 for receiving a bone fastener. The features of the opening 36 of the attachment member 14 are described below with reference to FIG. 1b.

Figure 1B:
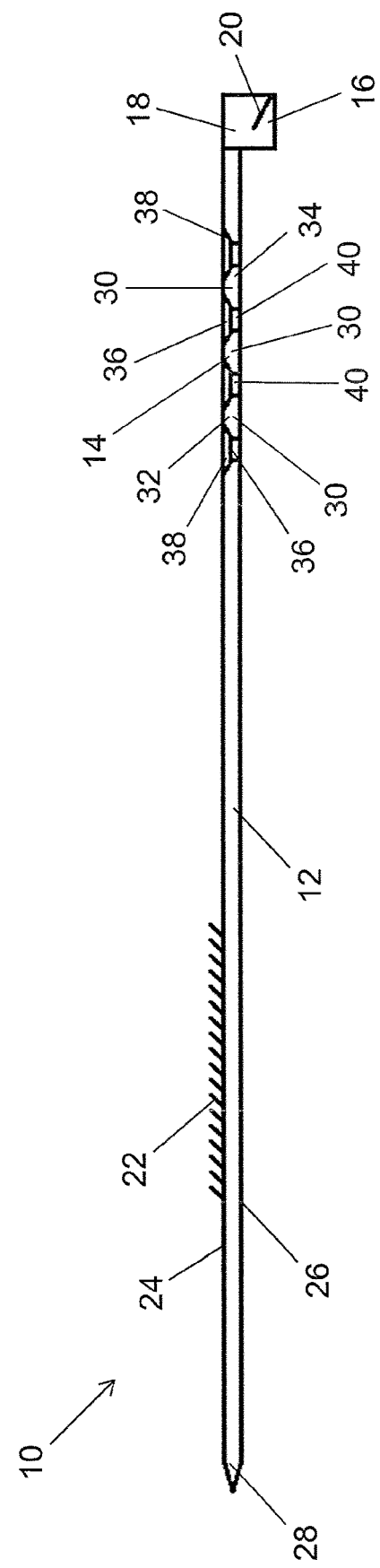

Referring to FIG. 1b, there is shown a cross-sectional side view of the first fixation assembly embodiment of FIG. 1a. It can be seen in FIG. 1b that each of the openings 36 of the attachment member 14 has a conical taper 38 which substantially tapers inwardly in a direction towards the bone contacting surface 26 of the attachment member 14 in a conical fashion. Alternatively, the at least one opening 36 of the attachment member 14 has a convex or spherical taper, i.e., has a curved shape. Further, each of the openings 36 of the attachment member 14 may have an inclined surface 38 onto which a bone fastener is able to slide in a fastening or compression position. The taper 38 may form a countersink. Moreover, the taper 38 may extend over the full circumference of the opening 36. Alternatively, the taper 38 may extend over an arc segment of the circumference of the opening 36. The taper 38 or the inclined surface 38 may be configured to receive a curved-shaped head of a bone fastener.

A cone angle of the taper 38 of each of the openings 36 of the attachment member 14 may generally be between 1 degree and 80 degrees, and is approximately 45 degrees in the present embodiment. Thus, each opening 36 of the attachment member 14 is, on the one hand, adapted to slidingly receive bone fasteners (such as sliding or compression screws), and, on the other hand, adapted to receive a locking screw or a cortical screw. In case of a locking screw, a threaded head thereof mates with the locking feature 40 of the opening 36 for providing an angularly stable locking engagement therebetween at a pre-defined angle (i.e., monoaxially).

As shown in FIGS. 1a and 1b, each opening 36 of the attachment member 14 is formed as a circular hole. Alternatively, at least one opening 36 of the attachment member 14 can be an elongated, e.g., an oblong hole.

In the present embodiment, each of the openings 36 of the attachment member 14 includes a locking feature 40. The locking feature 40 is configured to lock a bone fastener (not shown in FIGS. 1a and 1b) to the attachment member 14. The locking feature includes a threaded portion. In the present embodiment, the locking feature 40 of each opening 36 of the attachment member 14 is formed as a thread, e.g., a threaded hole portion. Alternatively, or in addition, the locking feature 40 may be formed as one or more circumferential lips, as a bayonet-type feature or otherwise. The threaded portion of the locking feature 40 is adapted to engage a bone fastener, e.g., engage a threaded head of a bone fastener. Thus, each of the openings 36 of the attachment member 14 can have a circumferential thread or is partially threaded.

As shown in FIG. 1b, each of the openings 36 includes an upper portion and a lower portion. The upper portion of each opening 36 is on the side 24 opposite to the bone contacting side 26. The lower portion of each opening 36 is at the bone contacting side 26. As can be seen in FIG. 1b, the upper portion defines taper 38. The lower portion includes the locking feature 40 in form of a thread to engage a bone fastener.

Each of the flexible elongated member 12 and the attachment member 14 has a thickness as shown in FIG. 1b. The thickness of the attachment member 14 is, in the present embodiment, substantially equal to the thickness of the flexible elongated member 12. Alternatively, the thickness of the attachment member 14 is larger than the thickness of the flexible elongated member 12.

The locking structure 16 of the flexible elongated member 12 has a thickness greater than the thickness of the flexible elongated member 12. Further, the locking structure 16 extends from the bone contacting side 26 away from the flexible elongated member 12. The pawl 20 is arranged within the locking structure 16 and extends from the inner surface of the through opening 18 of the latching mechanism inwardly into the through opening 18 as shown in FIG. 1b. As shown, the pawl 20 extends in a direction toward the flexible elongated member 12.

The teeth 22 of the flexible elongated member 12 are arranged on side 24 opposite to the bone contacting side 26. Further, the teeth 22 extend substantially away from the side 24 of the flexible elongated member 12 in a direction substantially toward the locking structure 16. Thus, each tooth 22 defines an angle with respect to the (upper) side 24 of the flexible elongated member 12. This angle can be between 1 degree and 90 degrees, and is preferably substantially 45 degrees. Therefore, each tooth 22 can interlock with the pawl 20 of the locking structure 16 to hold the fixation assembly around the sternum in a closed loop.

Referring to FIGS. 2a and 2b, there is shown a second embodiment of a fixation assembly 42 for securing parts of a sternum.

FIG. 2a illustrates a top view of the fixation assembly 42 and FIG. 2b illustrates a cross-sectional side view of the fixation assembly 42. The fixation assembly 42 includes the flexible elongated member 12 and the attachment member 14 and their configurations as described with reference to and as shown in FIGS. 1a and 1b. The only difference between the fixation assembly 10 shown in FIGS. 1a and 1b and the fixation assembly 42 of the present embodiment is the arrangement and the position respectively of the pawl 20 of the locking structure 16 and of the teeth 22 of the flexible elongated member 12.

In the present embodiment, the teeth 22 are arranged on a lateral surfaces, i.e., the side surfaces, of the flexible elongated member 12 as shown in FIG. 2a. Alternatively, the teeth 22 can only be arranged on one lateral surface of the flexible elongated member 12. Further, two pawls 16 are provided within the through opening 18 of the latching mechanism to engage on teeth 22 once they are snapped in place. As shown in FIG. 2a, the two pawls 16 facing each other are arranged on opposite sides of the locking structure 16. Alternatively, only one pawl 16 may be provided within the through opening 18 of the latching mechanism. In this case, the pawl 16 is arranged on that lateral surface or side of the locking structure 16 which corresponds to the lateral surface or side of the flexible elongated member 12 on which the teeth 22 are arranged.

Figure 3A:
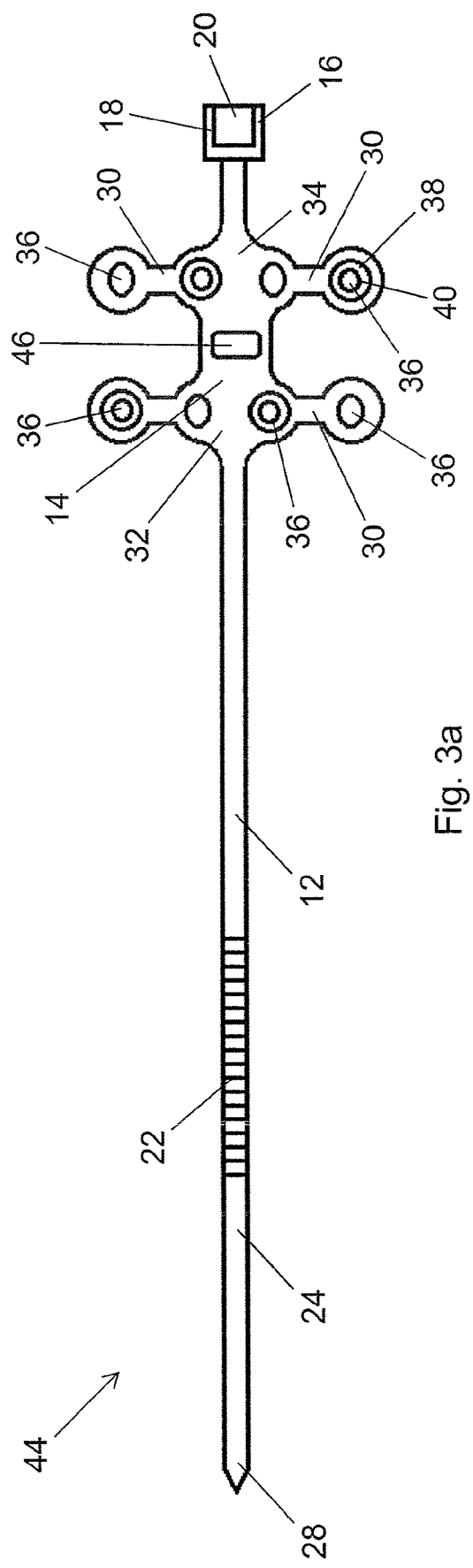
FIG. 3a is a top view of a fixation assembly according to a third embodiment.
Figure 3B:
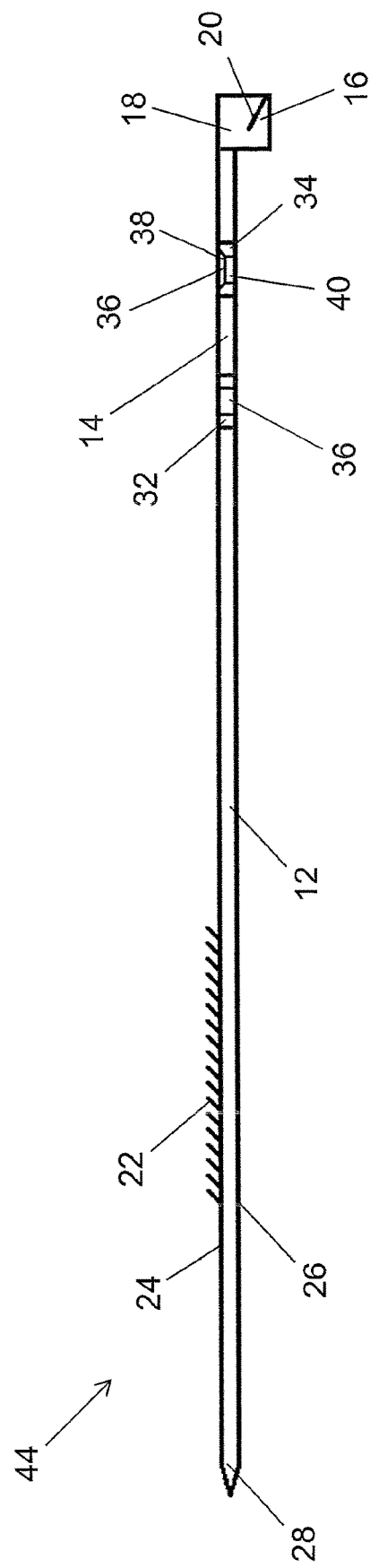

Referring to FIGS. 3a and 3b, there is shown a third embodiment of a fixation assembly 44 for securing parts of a sternum. FIG. 3a shows a top view of the fixation assembly 44 and FIG. 3b shows a cross-sectional side view of the fixation assembly 44.

The fixation assembly 44 includes the flexible elongated member 12 and the attachment member 14 and their configurations as described with reference to and as shown in FIGS. 1a and 1b. The only difference between fixation assembly 10 shown in FIGS. 1a and 1b and the fixation assembly 44 of the present embodiment is that the attachment member 14 has a longitudinal orientation which is substantially perpendicular to a longitudinal direction of the flexible elongated member 12. Further, the attachment member 14 of the fixation assembly 44 has multiple openings 36.

In the present embodiment, the attachment member 14 has multiple circular and elongated holes 36, e.g., four circular holes and four elongated holes. Each circular hole 36 includes a locking feature 40 and a taper 38 and is configured as generally described above with reference to and as shown in FIGS. 1a and 1b. Each elongated hole 36 may have an inclined surface onto which a bone fastener is able to slide in a fastening or compression position. As shown in FIG. 3a, each elongated hole 36 extends substantial parallel with respect to a longitudinal direction of the flexible elongated member 12. Thus, each of the elongated holes 36 of the attachment member 14 substantially extends along a line substantially perpendicular to a longitudinal direction of the attachment member 14. As can be further seen in FIG. 3a, each circular hole 36 (e.g., for receiving a bone fastener substantially perpendicular to bone of the attachment member 14) is arranged substantially aligned with an elongated hole 36 along the longitudinal direction of the flexible elongated member 12 or, respectively, along a line substantially perpendicular to a longitudinal direction of the attachment member 14. Alternatively, or in addition, each circular hole 36 having a locking feature 40 is arranged substantially aligned with an elongated hole 36 along the longitudinal direction of the attachment member 14. Thus, the attachment member 14 comprises an alternate arrangement of circular holes 36 having a locking feature 40 and elongated holes 36 for receiving, e.g., a compression screw.

As shown in FIG. 3a, the first and third hole of the first section 32 of the attachment member 14 and the second and fourth hole of the second section 34 of the attachment member 14 are elongated holes 36. The second and fourth hole of the first section 32 of the attachment member 14 and the first and the second hole of the second section 34 of the attachment member 14 are circular holes 36 having a locking feature 40 (e.g., for receiving a bone fastener substantially perpendicular to bone).

The attachment member 14 further includes in a central portion thereof a recess 46. The recess 46 has a substantially rectangular form. Alternatively, the recess 46 may have a circular or triangular form. Further, the recess 46 is used as a window for aligning the fixation assembly 42 correctly on the sternum by allowing a surgeon to view through the recess 46. Thus, the cutting line of the two sternum parts can be seen through recess 46 of the attachment member 14 which is then probably aligned on the two sternum parts.

Referring to FIGS. 4a to 4d, there is shown a fourth embodiment of a fixation assembly 48 for securing parts of a sternum.

Figure 4A:
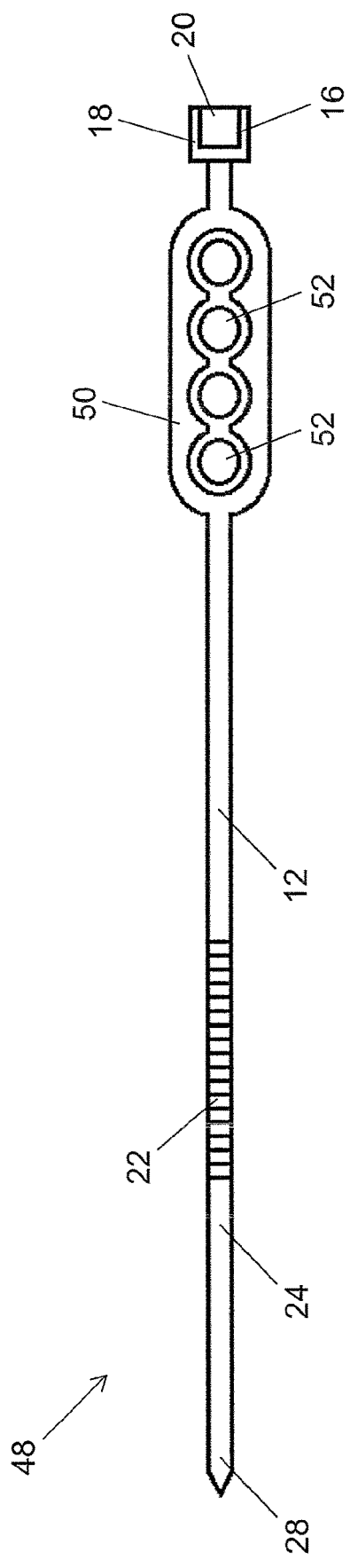
FIG. 4a is a top view of a fixation assembly according a fourth embodiment.
Figure 4B:
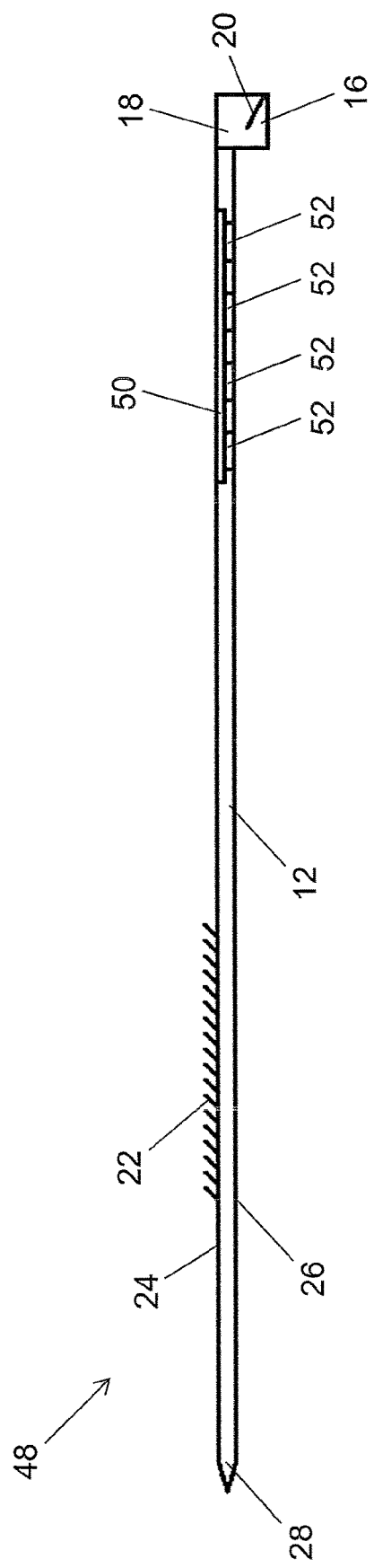

FIG. 4a shows a top view of the fixation assembly 48 and FIG. 4b shows a cross-sectional side view of the fixation assembly 48. Further, FIG. 4c shows a top view of an embodiment of the attachment member 14 and FIG. 4d shows a cross-sectional side view of thereof.

The fixation assembly 48 of the present embodiment includes the flexible elongated member 12 as configured and described with reference to and as shown in FIGS. 1a and 1b. The difference between the flexible elongated member shown in FIG. 1a and that of the present embodiment is that the flexible elongated member 12 has a receiving structure 50. The receiving structure 50 is configured to receive the attachment member 14. A further difference is that the attachment member 14 is formed as an insert. Thus, the attachment member 14 of the present embodiment is a separate part. The insert 14 can be inserted into the receiving structure 50. The attachment member 14 in form of an insert is shown in FIGS. 4c and 4d and is substantially configured and defined as generally described with reference to and as shown in FIGS. 1a and 1b.

As shown in FIGS. 4a and 4b, the receiving structure 50 includes at least one opening 52. In the present embodiment, the receiving structure 50 includes four openings 52 which are aligned along a longitudinal direction of the receiving structure 50. The shapes of the openings 52 of the receiving structure 50 are adapted to receive the attachment member 14 in a suitable manner. The receiving structure 50 may thus have an inner shape which substantially corresponds (i.e., mates with) the outer shape of the attachment member 14.

Figure 4C:
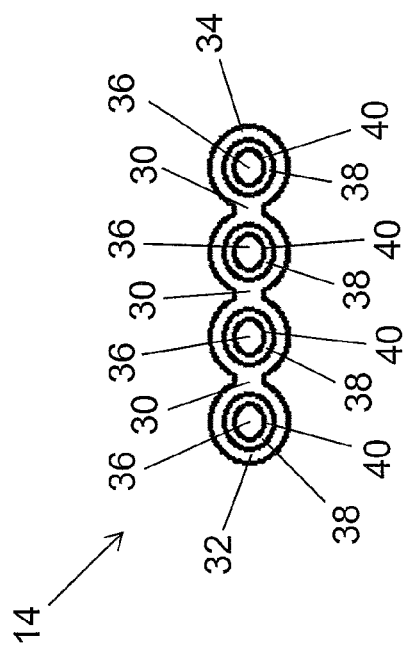
FIG. 4c is a top view of an insert embodiment.
Figure 4D:
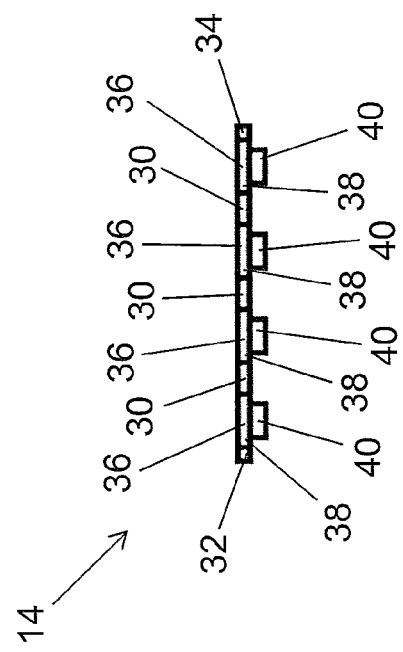
FIG. 4d is a cross-sectional view of the insert embodiment shown in FIG. 4c.

The attachment member 14 as shown in FIGS. 4c and 4d includes the openings 36 as described above with reference to FIGS. 1a and 1b. However, in the present embodiment, each opening 36 of the attachment member 14 is a circular hole. Further, each opening 36 has an upper cylindrical portion and a lower cylindrical portion as shown in FIG. 4d. The lower cylindrical portion includes the locking feature 40.

The attachment member 14 is, in the present embodiment, held in the receiving structure 50 by a from fit. The receiving structure 50 is configured to establish the holding of the attachment member 14 by a snap fit. This may be accomplished with a flexible or elatiscal protrusion (not shown in FIGS. 4a and 4b) of the receiving structure 50. Alternatively, the attachment member 14 is cast in the flexible elongated member 12.

Once the attachment member 14 in form of the insert is inserted in the receiving structure 50 of the flexible elongated member 12, the openings 52 of the receiving structure 50 substantially overlap with the openings 36 of the attachment member 14. Thus, a bone fastener can be inserted through the openings 36 of the attachment member 14 into bone.

As can be seen in FIG. 4b, the receiving structure 50 (or at least a part thereof) has a thickness which is substantially equal to a thickness of the flexible elongated member 12. Alternatively, at least a part of the receiving structure 50 or the entire receiving structure 50 has a thickness which is larger than a thickness of the flexible elongated member 12.

FIG. 5a shows a fifth embodiment of a fixation assembly 54 for securing parts of a sternum.

FIG. 5a illustrates a top view of a fixation assembly 54 having a detailed cross-sectional view of a part of the attachment member 14. The fixation assembly 54 comprises the flexible elongated member 12 as generally described with reference to as shown in FIGS. 1a and 1b. Further, the fixation assembly 54 includes the attachment member 14 as generally described with reference to and as shown in FIGS. 1a and 1b as well as FIGS. 3a and 3b.

In the present embodiment, the attachment member 14 includes multiple openings 36 for receiving bone fasteners. As shown in FIG. 5a, eight circular holes 36 each having a locking feature 40 in form of a thread are provided in attachment member 14. The attachment member 14 is also configured to be cut with a surgical tool such as a plier or cutting device. Thus, the number of openings 36 of the attachment member 14 can be adapted by cutting or trimming the attachment member 14 as generally described with reference to FIGS. 1a and 1b.

As shown in FIG. 5a, the attachment member 14 has multiple arms 56, in the present embodiment, four arms 56. The arms 56 of the attachment member 14 extend away from a central body of the attachment member 14. Further, the arms 56 have an undulating outer contour and include at least one opening 36 (here, two openings 36) for receiving bone fasteners. Thus, an outer peripheral surface of the arms 56 has an undulating shape, such that the arms 56 have a waisted shape. The attachment member 14 shown in FIG. 5a has a similar shape and configuration as the attachment member shown in FIG. 3a.

The difference between the attachment member 14 of the present embodiment shown in FIG. 5a and that shown and described with reference to FIGS. 1a and 3a is that the attachment member 14 is slideably coupled to the flexible elongated member 12. Thus, the attachment member 14 of the present embodiment is a separate part. For this purpose, the attachment member 14 includes a guiding structure 58 for slideably engaging the flexible elongated member 12. As shown in FIG. 5a, the guiding structure 58 is substantially oriented along a line which is substantially perpendicular to the longitudinal direction of the attachment member 14. Thus, the guiding structure 58 extends substantially along the longitudinal axis of the flexible elongated member 12. The guiding structure 58 receives the flexible elongated member 12 in a slideable manner. The attachment member 14 can thus slide along the flexible elongated member 12 in the direction of the longitudinal axis of the flexible elongated member 12. Hence, during implantation of the fixation assembly 54, the attachment member 14 can be exactly aligned on the two parts of the sternum by sliding the attachment member 14 on the flexible elongated member 12.

The guiding structure 58 of the attachment member 14 may have different forms, e.g., as shown in FIGS. 5b, 5c and 5d. The guiding structure 58 of the attachment member 14 is formed as a recess 60 or an opening 60.

In the embodiment shown in FIG. 5b, the recess 60 is formed as a groove 60. The groove 60 of the guiding structure 58 can receive the flexible elongated member 12, e.g. the flat band thereof, such that the attachment member 14 can slide along the surface of the flexible elongated member 12. Further, the groove 60 of the guiding structure 58 has a stepped configuration as shown in FIG. 5b. The groove 60 thus has two (or more) different lateral dimensions. As can be seen in FIG. 5b, the groove 60 includes an upper groove section having a smaller width and a lower groove section having a larger width. Each of these groove sections may receive a flexible elongated member 12.

FIG. 5c shows another embodiment of the guiding structure 58. In this embodiment, the guiding structure 58 also includes a recess 60. However, the recess 60 is here formed as a groove having a T-form in cross-section. As shown in FIG. 5c, two protrusions 62 of the guiding structure 58 define the T-shaped grooved 60. Further these protrusions 62 captively held the flexible elongated member 12 in a direction substantially perpendicular to the sliding direction of the attachment member 14 (i.e., to the longitudinal direction of the flexible elongated member 12).

FIG. 5d illustrates a further embodiment of the guiding structure 58. In this embodiment, the recess 60 of the guiding structure 58 is formed as an opening 60, i.e., a through opening. The opening 60 of the guiding structure 58 has in cross-section a form of an elongated or oblong hole. Further, the opening 60 of the guiding structure 58 extends substantially through the attachment member 14. The opening 60 may also receive the flexible elongated member 12 in a slideable manner along the longitudinal direction of the flexible elongated member 12.

FIGS. 6a and 6b show a sixth embodiment of a fixation assembly 64 for securing parts of a sternum.

FIG. 6a illustrates a top view of the fixation assembly 64 and FIG. 6b illustrates a cross-sectional side view of the fixation assembly 64. The fixation assembly 64 comprises the flexible elongated member 12 and the attachment member 14 as generally described with reference to and as shown in FIGS. 1a and 1b.

The difference between the fixation assembly 64 shown in FIG. 6a and the fixation assembly 10 as shown in FIG. 1a is that the attachment member 14 is, in the present embodiment, formed as a mesh. The mesh is integrally formed with the flexible elongated member 12. Alternatively, the mesh can also be a separate part (e.g., an insert) from the flexible elongated member 12.

The attachment member 14 formed as a mesh includes at least one or multiple openings 36 for receiving bone fasteners. In the present embodiment, the attachment member 14 includes five openings 36. These openings 36 of the attachment member 14 are substantially arranged along the longitudinal axis (direction) of the attachment member 14. Further, each of the opening 36 includes a locking feature 40 and a taper 38 as generally described above with reference to FIGS. 1a and 1b. Alternatively, at least one of these openings 36 may have a cortical or convex taper (e.g., an inclined surface) onto which a bone fastener is able to slide in a compression position or fastening position. As shown in FIG. 6a, the openings 36 of the attachment member 14 are all circular holes. However, also elongated holes can be provided in the mesh structure of the attachment member 14. Each of the openings 36 of the attachment member 14 is connected to another opening 36 via at least one bridge 30. The bridges 30 can be straight or curved as shown in FIG. 6a. Thus, the attachment member 14 may have an undulating outer shape. In the present embodiment, an outer peripheral surface of the attachment member 14 has an undulating shape, such that the attachment member 14 has a waisted shape. Alternatively, or in addition, the attachment member 14 may have a straight outer contour.

Each of the bridges 30 of the mesh of the attachment member 14 is configured to be cut with a surgical tool, such as a plier or a cutting device. Further, each of the bridges 30 may also have the configuration as generally described above with reference to and as shown in FIGS. 1a and 1b. At least two bridges 30 are arranged parallel to each other as shown in FIG. 6a. Further, two openings 36 arranged adjacent to each other and two curved bridges 30 opposite to each other form a recess 66. The recess 66 has substantially the form of a barbell as shown in FIG. 6a.

Figure 7:
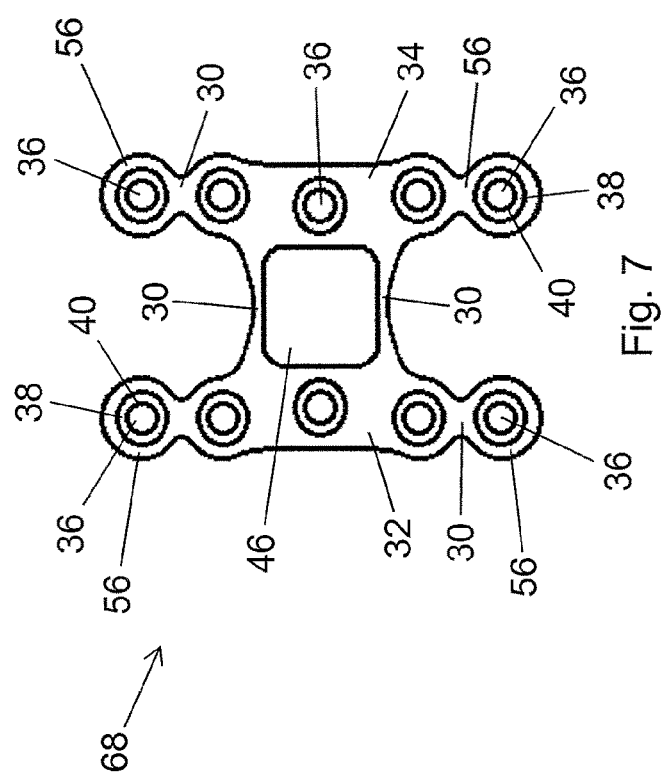
FIG. 7 is a top view of a further attachment member embodiment.

FIG. 7 shows a top view of a further attachment member embodiment 68. The further attachment member 68 has substantially the configuration of the attachment member 14 as described above and hereinafter.

The further attachment member 68 is formed as a bone plate. Alternatively, the further attachment member 68 may be formed as a mesh, e.g., a mesh as generally described with reference to and as shown in FIG. 6a. The further attachment member 68 is, in the present embodiment, made from titanium. Alternatively, or in addition, the further attachment member 68 can be made from at least one of an alloy of titanium, stainless steel, polyetheretherketone (PEEK) and a resorbable material.

As can be seen from FIG. 7, the further attachment member 68 includes a first section 32 configured to be secured to the sternum and a second section 34 configured to be secured to the sternum as generally described with reference to FIGS. 1a, 1b, 3a and 3b. Each of the first section 32 and the second section 34 of the further attachment member 68 has at least one opening 36 for receiving a bone fastener. In the present embodiment, the further attachment member 68 includes multiple openings 36 for receiving bone fasteners. Each of the openings 36 of the further attachment member 68 may be configured as generally described with reference to and as shown in FIGS. 1a and 1b as well as FIGS. 3a and 3b.

Moreover, each of the openings 36 of the further attachment member 68 has a conical, convex or spherical taper 38 which substantially tapers inwardly in a direction toward a bone facing surface of the further attachment member 68. The bone facing surface is a surface of the further attachment member 68 which faces toward bone. Thus, the bone facing surface of the further attachment member 68 substantially corresponds to a bone contacting surface. Further, each of the openings 36 of the further attachment member 68 may have an inclined surface (e.g., taper 38) onto which a bone fastener is able to slide in a fastening or compression position. The taper 38 may form a countersink. Moreover, the taper 38 may extend over the full circumference of the opening 36. Alternatively, the taper 38 may extend over an arc segment of the circumference of the opening 36. The taper 38 or the inclined surface 38 may be configured to receive a curved-shaped head of a bone fastener. As can be seen from FIG. 7, each opening 36 of the further attachment member 68 is a circular hole. Alternatively, or in addition, at least one opening 36 may be an elongated hole.

In the present embodiment as shown in FIG. 7, each opening 36 of the further attachment member 68 includes a locking feature 40 configured to lock a bone fastener to the further attachment member 68. The locking feature 40 of each opening 36 of the further attachment member 68 has a configuration as generally described with reference to and as shown in FIGS. 1a and 1b. Thus, in the present embodiment, the locking feature 40 includes a threaded portion adapted to engage a bone fastener. In detail, each opening 36 of the further attachment member 68 includes a threaded for matingly engaging a threaded head of a bone fastener. Alternatively, at least one of the openings 36 of the further attachment member 68 includes one or more circumferential lips adapted to engage a bone fastener.

As shown in FIG. 7, the further attachment member 68 includes at least one bridge 30 which is configured to be cut with a surgical tool, such as a plier or cutting device. In the present embodiment, the further attachment member 68 includes two bridges 30. Thus, the further attachment member 68 is configured to be cut with a surgical tool, e.g., into two pieces, if it is necessary when a complication takes place after the implantation of the fixation assembly and the further attachment member 68. The further attachment member 68 includes multiple bridges 30. In the present embodiment, the further attachment member 68 has two bridges 30. As shown in FIG. 7, the two bridges 30 of the further attachment member 68 connect the first section 32 and the second section 34 to each other. Further, the two bridges 30 are arranged parallel to each other.

As can be seen in FIG. 7, the further attachment member 68 includes a recess 46 used as a window as generally described with reference to and as shown in FIG. 3a. Thus, a surgeon can exactly align the further attachment member 68 on the sternum by viewing through this recess 46. The recess 46 of the further attachment member 68 has a substantially rectangular form. Alternatively, the recess 46 may have a triangular or circular shaped form. As can be seen from FIG. 7, the two bridges 30 and the first and second sections 32, 34 of the further attachment member 68 define the recess 46.

The further attachment member 68 further includes a receiving structure (not shown in FIG. 7) configured to receive a part of a fixation assembly. The receiving structure of the further attachment member may thus receive part of the first elongated member 12 or the attachment member 14 of one of the fixation assemblies described above or hereinafter. The receiving structure of the further attachment member 68 is arranged on the bone facing side of the further attachment member 68. The further attachment member 68 can therefore be placed on top of the fixation assembly. The receiving structure may be a groove or recess. Further, the receiving structure may substantially extend in a direction of the longitudinal direction of the flexible elongate member 12 or a long a line with is substantially perpendicular to the longitudinal direction of the further attachment member 68.

Figure 8:
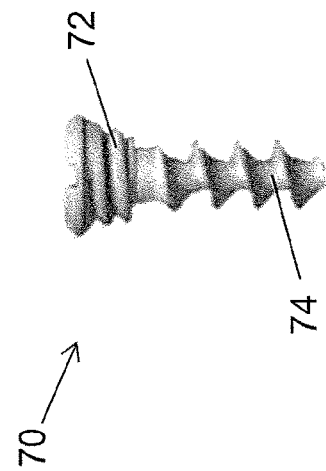
FIG. 8 is a perspective view of a bone fastener embodiment.

FIG. 8 shows an embodiment of a bone fastener 70. The bone fastener 70 is in form of a bone screw having a head 72 and a shaft 74. The head 72 of the bone fastener 70 has a thread. The thread of the head 72 of the bone fastener 70 is configured to engage a thread 40 of one of the openings 36 of the attachment member 14. As can be seen in FIG. 8, the head 72 of the bone fastener 70 has a conical outer shape. Alternatively, the head 72 may have a curved, e.g. convex or spherical, outer shape.

The shaft 74 of the bone fastener 70 has a thread for engaging bone (e.g., a cancellous thread). In the present embodiment, the bone fastener 70 is formed as a locking screw. Alternatively, the bone fastener can be a cortical screw, a compression screw or a bone peg.

A fixation system for securing parts of a sternum may comprise a fixation assembly as previously described with reference to FIGS. 1a to 6b and at least one bone fastener 70 as generally described with reference to and as shown in FIG. 8.

Figure 9A:
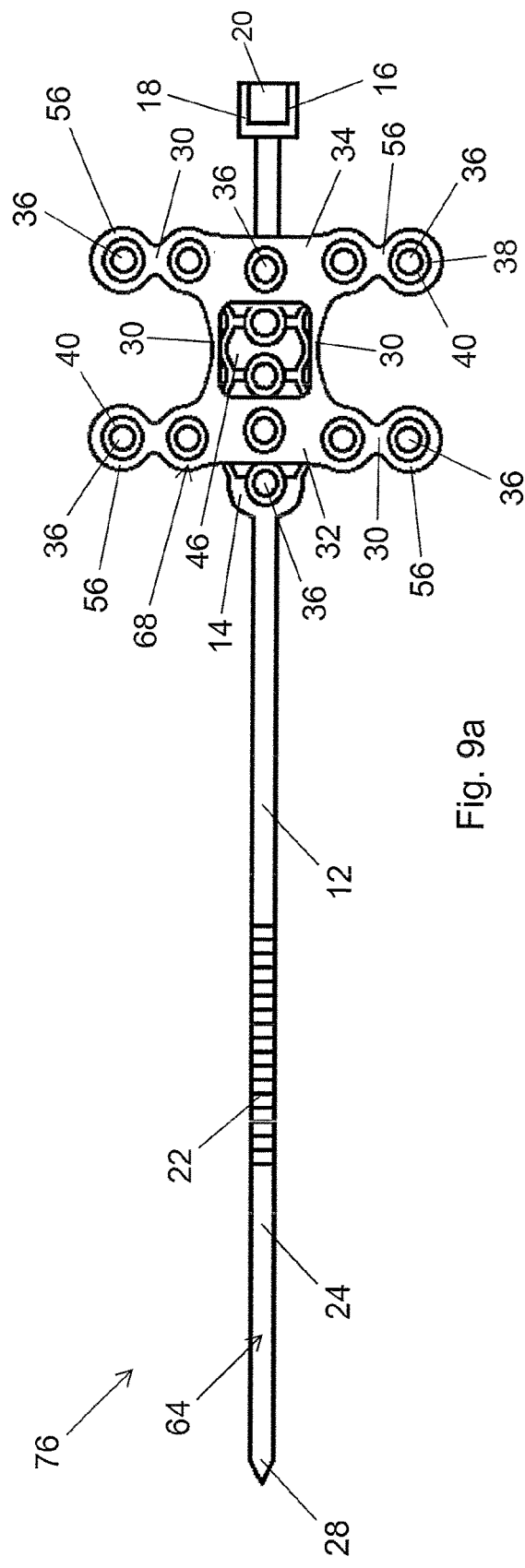
FIG. 9a is a top view of a fixation system embodiment having the fixation assembly shown in FIGS. 6a and 6b and the further attachment member embodiment shown in FIG. 7.

FIG. 9a illustrates a top view of a fixation system 76 for securing parts of a sternum. The fixation system 76 comprises the fixation assembly 64 as generally described with reference to and as shown in FIGS. 6a and 6b. Alternatively, the fixation system 76 may include any previously described fixation assembly, e.g., as shown in FIGS. 1a to 5a. Moreover, the fixation system 76 comprises the further attachment member 68 as described with reference to and as shown in FIG. 7.

As shown in FIG. 9a, the further attachment member 68 is arranged on top of the fixation assembly 64. In this case, the receiving structure of the further attachment member 68 receives a part of the fixation assembly 64 at the bone facing side of the further attachment member 68. Alternatively, when the further attachment member 68 may not include such a receiving structure, the further attachment member 68 is just placed on top of the fixation assembly.

As can be seen from FIG. 9a, two of the openings 36 of the further attachment member substantially overlap with two openings 36 of the attachment member 14 of the fixation assembly 64. In detail, one opening 36 of the first section 32 of the further attachment member 68 substantially coincides with one opening 36 of the first section 32 of the attachment member 14 of the fixation assembly 64. Further, one opening 36 of the second section 34 of the further attachment member 68 substantially coincides with one opening 36 of the second section 34 of the attachment member 14 of the fixation assembly 64. Moreover, each of the two bridges 30 of the further attachment member 68 substantially overlaps with at least one bridge 30 of the attachment member 14 of the fixation assembly 64. Thus, the pair of bridges 30 of the attachment member 14 of the fixation assembly 64 and the further attachment member 68 can be cut with a surgical tool within one single cutting step.

Figure 9B:
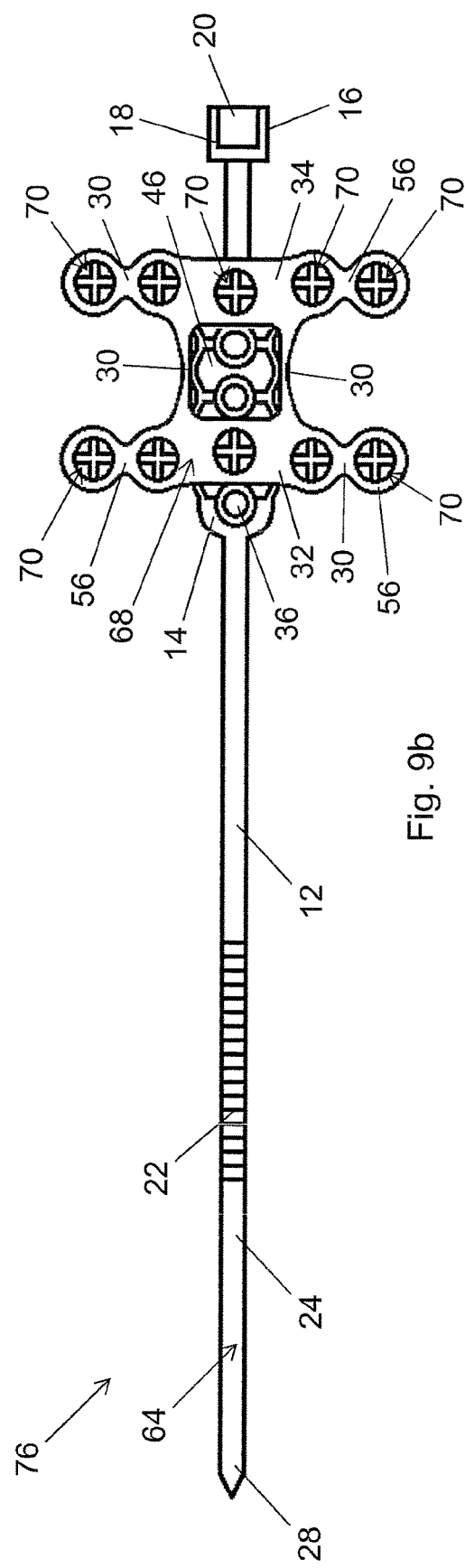
FIG. 9b is a top view of the fixation system embodiment shown in FIG. 9a with bone fastener embodiments shown in FIG. 8.

FIG. 9b is a top view of the fixation system 76 as shown in FIG. 9a including bone fasteners 70 as described with reference to and as shown in FIG. 8. In the present embodiment, the bone fasteners 70 are locking screws as illustrated in FIG. 8.

As can be seen from FIG. 9b, each opening 32 of the further attachment member 68 can receive a bone fastener 70. The bone fasteners 70 which are inserted through the two openings 36 of the further attachment member 68 which coincide with openings 36 of the attachment member 14 of the fixation assembly 64 are configured to fasten the further attachment member 68 to the fixation assembly 64. Further, since the bone fasteners 70 are locking screws with a threaded head for engaging on the locking feature 40 of each opening 36 of the further attachment member 68, the bone fastener 70 can be locked to the further attachment member 68.

Alternatively, or in addition, the fixation system 76 may comprise a surgical tool for cutting the bridges 30, the further attachment member 68 and/or the attachment member 14. The surgical tool can be a cutting device, a plier or surgical scissor.

Figure 10:
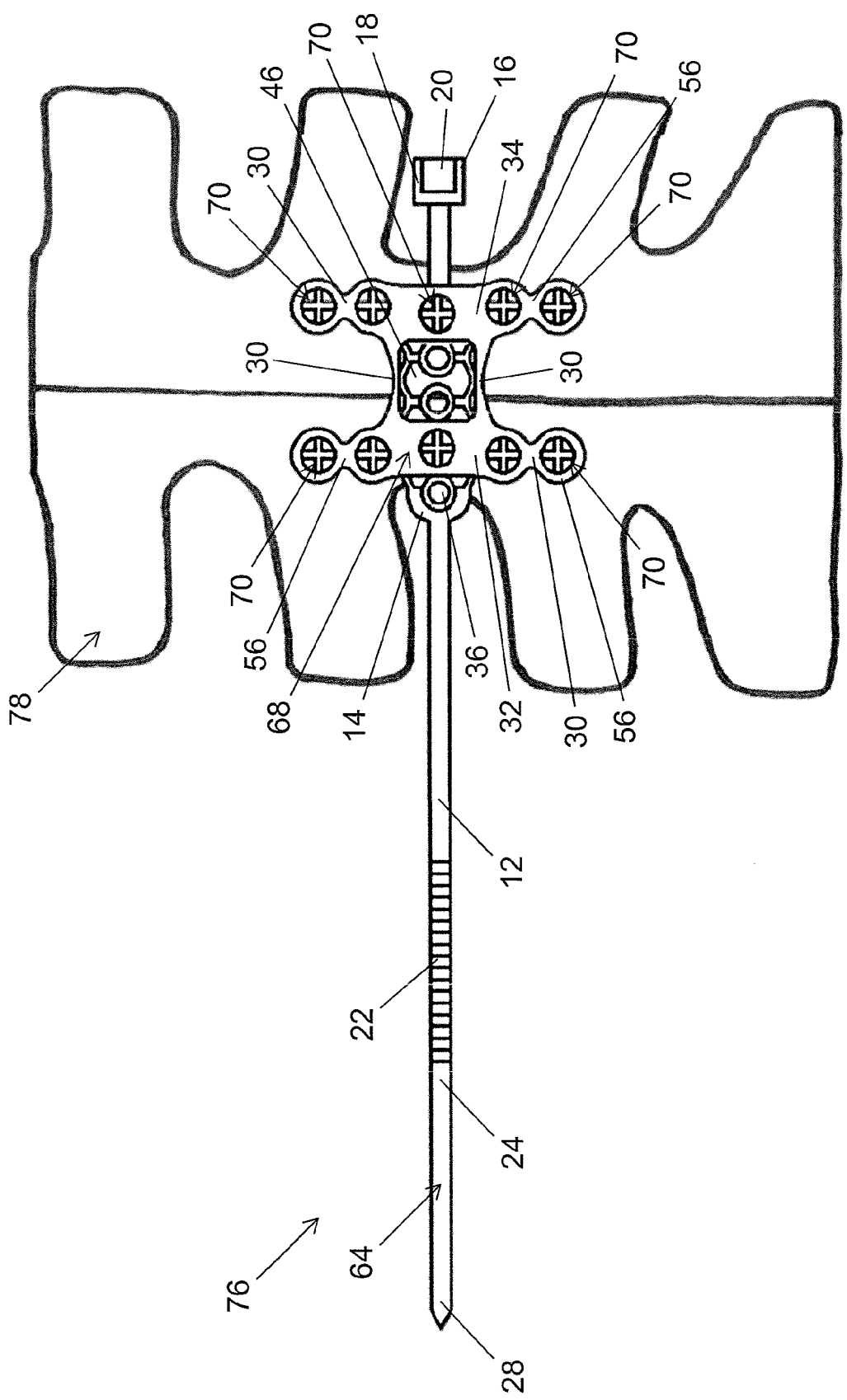
FIG. 10 shows the fixation system embodiment of FIG. 9b attached on a sternum of a patient.

FIG. 10 shows the fixation assembly 76 shown in FIGS. 9a and 9b that has been attached to a sternum 78 with bone fasteners 70.

The two sternum parts that had been separated by a bone cut have been brought back to their initial position and secured by the fixation assembly 64. The fixation assembly 64 is firstly looped around the two sternum parts. Then, the attachment member 14 is properly aligned on the two sternum parts. The fixation assembly 64 is then tightened by inserting the needle shaped end of the flexible elongated member 12 through the through opening 18 of the locking structure 16 of the fixation assembly 64. Then, the fixation assembly 64 is fixed by locking the teeth 22 of the flexible elongated member 12 of the fixation assembly 64 to the locking structure 16 of the fixation assembly 64. If necessary, the attachment member 14 of the fixation assembly 64 is fixed to the sternum parts by inserting bone fasteners 70 through the openings 36 of the attachment member 14 of the fixation assembly 64. Alternatively, or in addition, the further attachment member 68 is placed on top of the fixation assembly 64 as shown in FIG. 10. The further attachment member 68 is then locked to the fixation assembly 64 and/or fixed to the sternum 78 by bone fasteners 70 inserted through the openings 36 of the further attachment member 68. In this case, as illustrated in FIG. 10, the first section 32 of the further attachment member 68 (and, optionally, of the attachment member 14 of the fixation assembly 64) is attached to one sternum part and the second section 34 of the further attachment member 68 (and, optionally, of the attachment member 14 of the fixation assembly 64) is attached to the other sternum part.

During a period of coughing, a force acting on sternum 78 in a lateral direction thereof may be up to 1500 Newton (N). It is therefore desired to maintain the initial secured relative orientation of the sternum parts, even when the sternum 78 is subjected to forces of this magnitude.

The closed configuration of the fixation assembly prevents relative displacement of the sternum parts in the lateral direction of the sternum 78 due to the flexible elongated member 12 looped around the sternum parts and, if necessary, also due to the attachment member 14 of the fixation assembly and/or the further attachment member 68 fixed to the sternum 78 by bone fasteners 70. The fixation assembly and the further attachment member hold the two sternum parts in an abutting relationship. By the provision of openings 36 configured as elongated holes, inclined holes or holes having an inclined surface or taper onto which a bone fastener is able to slide in a fastening or compression position, the sternum parts can be additionally compressed in the lateral direction upon tightening the associated bone fasteners.

Figure 11:
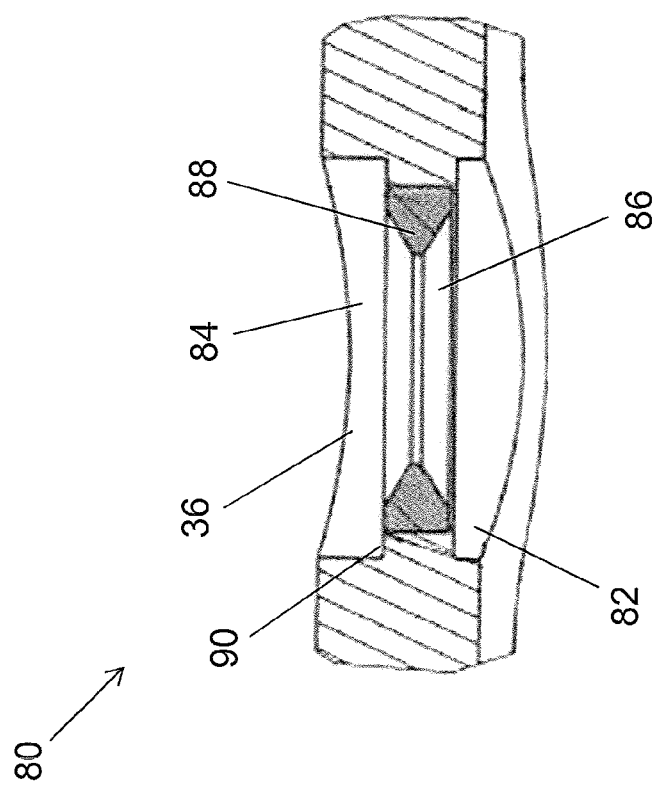
FIG. 11 is a cross-sectional view of an alternative locking screw hole embodiment.

Referring to FIG. 11, there is shown a further embodiment 80 of an opening 36 in form of a locking screw hole 36 for an attachment member as discussed herein. The locking screw hole 36 includes a lower cylindrical hole portion 82 on the bone contacting side of the attachment member and an upper cylindrical hole portion 84 on the side opposite to the bone contacting side. A middle portion 86 is arranged between the upper and lower cylindrical hole portion 82, 84. The middle portion 86 includes a circumferential lip 88 having roughly the cross-sectional shape of a triangle. Thus, in this embodiment, the locking feature 40 of the opening 36 is formed as a circumferential lip 88. A bone fastener 70 (not shown in FIG. 11) can be polyaxially inserted through the locking screw hole 36, wherein the bone fastener 70 lockingly engages the circumferential lip 88. As further illustrated in FIG. 11, a diameter of the middle portion 86 is smaller than each of a diameter of the upper cylindrical portion 84 and a diameter of the lower cylindrical portion 82. Moreover, the locking screw hole 36 includes a supporting structure 90 defined by the upper cylindrical portion 84. The supporting structure 90 may receive a head portion of a bone fastener 70 (not shown in FIG. 11).

Figure 12:
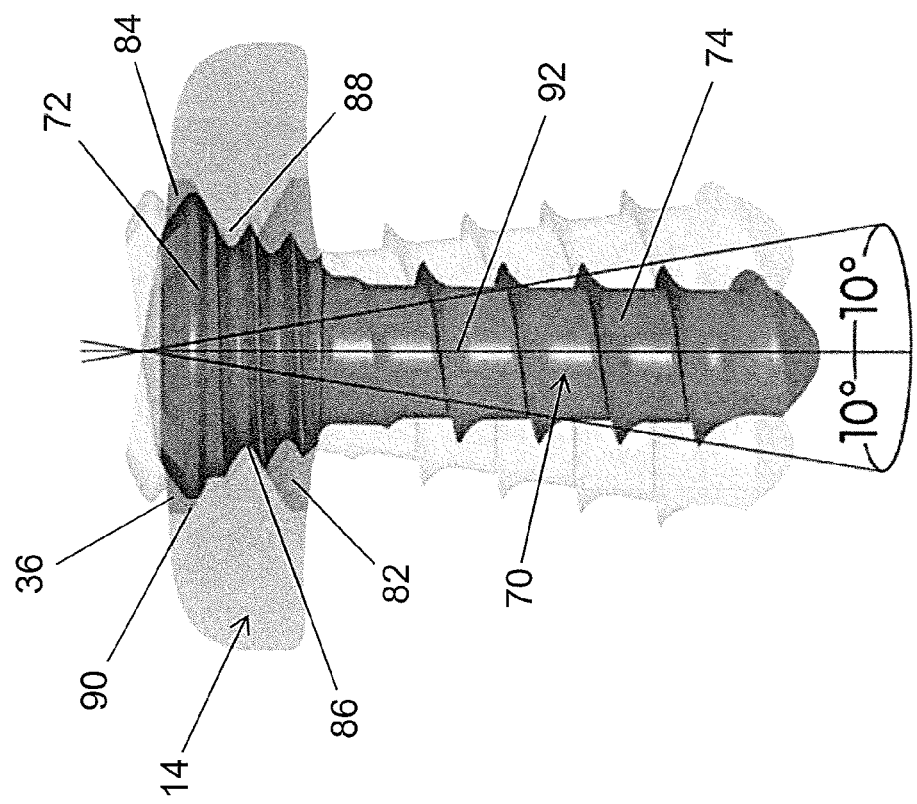
FIG. 12 is a view of the bone fastener embodiment shown in FIG. 8 inserted in the alternative locking screw hole embodiment of FIG. 11.

FIG. 12 shows a view of the bone fastener embodiment 70 shown in FIG. 8 inserted in the alternative locking screw hole embodiment 80 shown in FIG. 11.

As can be seen in FIG. 12, the bone fastener 70 can be inserted in the locking screw hole 36 at different angles relative to a central axis 92 of the locking screw hole 36. Thus, an insertion angle of the bone fastener 70 may vary from about 0 to about 45 degrees (e.g., from about 0 to about 10 degrees) relative to the central axis 92 of the locking screw hole 36.

The thread of the head 72 of bone faster 70 is configured to engage on the circumferential lip 88 which has roughly the cross-sectional shape of a triangle. The bone fastener 70 can thus be polyaxially inserted through the locking screw hole 36, wherein the bone fastener 70 lockingly engages the circumferential lip 88.

Figure 13:
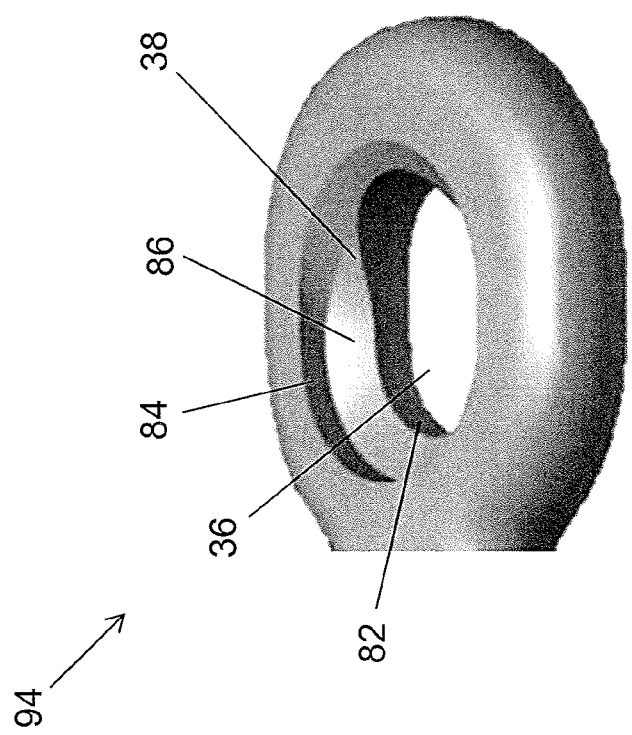
FIG. 13 is a perspective view of an alternative hole embodiment.

Referring to FIG. 13 there is shown is a perspective view of a further embodiment 94 of an opening 36 in form of a sliding screw hole 36 for an attachment member as discussed herein. In the present embodiment, the sliding screw hole 36 is formed as an elongated (e.g., oblong) hole.

The sliding screw hole 36 includes a lower cylindrical hole portion 82 on the bone contacting side of the attachment member and an upper cylindrical hole portion 84 on the side opposite to the bone contacting side. In the present embodiment, the upper cylindrical hole portion 84 extends over an arc segment of the circumference of the sliding screw hole 36 as shown in FIG. 13. The upper cylindrical hole portion 84 may extend over about 160 to about 260 degrees (e.g. about 160 to about 200 degrees), and in the present embodiment about 180 degrees.

The lower cylindrical hole portion 82 may include the locking feature 40 as generally described above. Thus, the lower cylindrical hole portion 82 may have a thread 40 or circumferential lip 88 configured to engage on a thread head 72 of a bone fastener 70 (not shown in FIG. 13).

A middle portion 86 is arranged between the upper and lower cylindrical hole portion 82, 84. The middle portion 86 includes a taper which substantially tapers inwardly in a direction toward a bone contacting surface of the attachment member in a conical fashion. In the present embodiment, the middle portion 86 also extends over an arc segment of the circumference of the sliding screw hole 36 as shown in FIG. 13. The middle portion 86 may extend over about 160 to about 260 degrees, e.g. about 160 to about 200 degrees, and in the present embodiment about 180 degrees. The middle portion 86 may also include the locking feature 40 as generally described above. Thus, the middle portion 86 may have a thread 40 or circumferential lip 88 configured to engage on a thread head 72 of a bone fastener 70 (not shown in FIG. 13).

The sliding screw hole 36 further includes an inclined surface 38 onto which a bone fastener 70 is able to slide in a fastening or compression position. Thus, the sliding screw hole 36 may permit a bone fastener 70 to slide laterally or longitudinally with respect to the sliding screw hole 36. Further, the sliding screw hole 36 may define a predetermined direction for a bone fastener 70. The inclined surface 38 has a predetermined angle with respect to an extension plane of the attachment member or with respect to the central axis of the sliding screw hole 36. The predetermined angle can be between about 20 and 70 degrees, for example about 40 to 50 degrees, and is, in the present embodiment, about 45 degrees. Moreover, the inclined surface 38 extends over an arc segment of the circumference of the sliding screw hole 36. Alternatively, the inclined surface 38 may extend over the full circumference of the sliding screw hole 36. The sliding screw hole 36 may include two or more inclined surfaces 38 onto which a bone fastener 70 is able to slide in a fastening or compression position. One inclined surface 38 may be arranged within sliding screw hole 36 opposite a further inclined surface 38. Thus, two inclined surfaces 38 may be arranged facing each other. The inclined surface 38 is configured to receive a curved or conical shaped head of a bone fastener 70. The bone fastener 70 may be a sliding screw, e.g., a compression screw.

Thus, a bone fastener 70 is able to slide (e.g., laterally or longitudinally) on the inclined surface 38 in a fastening or compression position. The sliding screw hole 36 is thus configured to exert a force on the attachment member when a bone fastener 70 is screwed or inserted through the sliding screw hole 36 into the sternum. Once, a bone fastener 70 in form of a locking screw inserted through the sliding screw hole 36 has reached a fastening position, the threaded head 72 of locking screw 70 lockingly engages the locking feature 40 (e.g., a thread or circumferential lip) of the lower cylindrical hole portion 82 of the sliding screw hole 36. Alternatively, when a bone fastener 70 in form of a sliding or compression screw inserted through the sliding screw hole 36 has reached a compression position, the conical or curved head of bone fastener 70 abuts against the taper of the middle portion 86 of the sliding screw hole 36.

As described above, each of the first and second section 32, 34 of the attachment member 14 or the further attachment member 68 may include an opening 36 for receiving a bone fastener (e.g., a sliding screw hole 36 as described above with reference to and as shown in FIG. 13). Thus, at least one sliding screw hole 36 may be arranged in the first section 32 and at least one sliding screw hole 36 may be arranged in the second section 34 of the attachment member 14, 68. The sliding screw holes 36 of the first and second section 32, 34 may be arranged opposite to each other. Further, the sliding screw holes 36 of the first and second section 32, 34 may be facing each other. The inclined surfaces 36 of the sliding screw holes 36 of the first and second section 32, 34 may extend substantially in a direction of the longitudinal axis of the attachment member 14, 68 or substantially perpendicular thereto. Hence, the inclined surfaces 36 may substantially extend towards a cutting line of the sternum halves.

In one implementation, the sliding screw holes 36 of the first and second section 32, 34 may be arranged mirror-inverted with respect to a mirror axis. The mirror axis can be defined by the longitudinal axis of the attachment member 14, 68 or a line substantially perpendicular thereto. Thus, the mirror axis may extend substantially along a cutting line of the sternum halves.

Consequently, a bone fastener 70 is able to slide on the inclined surface 38 of one of the sliding screw hole 36 substantially in a direction towards the cutting line of the sternum halves in a fastening or compression position. Thereby, the sternum halves are compressed to each other. The sliding screw hole 36 is thus configured to exert a force on the attachment member and therewith on the two sternum halves when a bone fastener 70 is screwed or inserted through the sliding screw hole 36 into the sternum.

The flexible elongated member 12 and attachment member 14 of the fixation assemblies and/or the further attachment member as described above, can be adapted to different sternum applications and may thus have different holes and a different shape. Thus, the flexible elongated member and the attachment members can be adapted as needed (e.g., in terms of shape, length, width, thickness, etc.) for use in orthopedic surgery for fixation of sternum bone, in particular, for securing at least two parts of a sternum together. Further, while many of the openings shown herein are circular, they could be elongated as well.

While the bone fasteners as described and shown herein are formed as locking screws, the bone fasteners can be of any type (e.g., cortical screws, compression screws, sliding screws, bone pegs, guide bushings, any kind of blade or wire-like fasteners) and can be adapted to different applications as needed. The bone fasteners may thus have different diameters, length, shapes or threads. Further, the fasteners and the implants described above can generally be made of stainless steel, titanium or any other biocompatible material.

While the above embodiments have exemplary been described in relation to bone screws, bone plates and meshes, it will be readily apparent that the techniques presented herein can also be implemented in combination with other types of bone fasteners (such as bone pegs having a rod-like or pin-like shaft, wire-like bone fasteners, etc.) as well as other types of implants (such as nails, bone distractors, etc.). Accordingly, the present disclosure is not limited to any type of bone fastener or any type of implant.

The features described in the above description taken in conjunction with the accompanying drawings can be readily combined to result in different embodiments. It will thus be apparent that the present disclosure may be varied in many ways. Hence, any described features may be used in all possible combinations. Such variations are not to be regarded as a departure from the scope of the disclosure, and all modifications are intended to be included within the scope of the following claims.

The invention claimed is:

1. A fixation assembly for securing parts of a sternum, the assembly comprising:
    a flexible elongated member including a locking structure configured to secure the flexible elongated member in a loop around the sternum parts; and
    an attachment member having at least one opening for receiving a bone fastener, wherein the attachment member is coupled to the flexible elongated member, wherein the attachment member is cast in the flexible elongated member.

2. The fixation assembly according to claim 1, wherein the flexible elongated member and the attachment member are integrally formed.

3. The fixation assembly according to claim 1, wherein the flexible elongated member is made from at least one of titanium, an alloy of titanium, stainless steel, polyetheretherketone (PEEK) and a resorbable material, and the attachment member is made from at least one of titanium, an alloy of titanium, stainless steel, polyetheretherketone (PEEK) and a resorbable material.

4. The fixation assembly according to claim 1, wherein each of the flexible elongated member and the attachment member defines a width in a transverse direction thereof, wherein the width of the attachment member is larger than or substantially equal to the width of the flexible elongated member.

5. The fixation assembly according to claim 1, wherein each of the flexible elongated member and the attachment member has a thickness, wherein the thickness of the attachment member is larger than or substantially equal to the thickness of the flexible elongated member.

6. The fixation assembly according to claim 1, wherein a longitudinal orientation of the attachment member is substantially perpendicular to a longitudinal direction of the flexible elongated member.

7. The fixation assembly according to claim 1, wherein the locking structure of the flexible elongated member is arranged at or near one end of the flexible elongated member.

8. The fixation assembly according to claim 1, wherein the locking structure of the flexible elongated member includes a latching mechanism configured to lock the flexible elongated member in a loop configuration.

9. The fixation assembly according to claim 8, wherein the flexible elongated member includes teeth, barbs or claws arranged along a longitudinal direction of the flexible elongated member and lockable with the latching mechanism.

10. The fixation member according to claim 1, wherein the attachment member includes:
    a first attachment section having at least one opening for receiving a bone fastener and being configured to be secured to the sternum; and
    a second attachment section having at least one opening for receiving a bone fastener and being configured to be secured to the sternum.

11. The fixation assembly according to claim 10, wherein the attachment member includes at least one bridge configured to connect the first attachment section and second attachment section to each other and configured to be cut with a surgical tool.

12. The fixation assembly according to claim 11, wherein the attachment member includes multiple bridges.

13. The fixation assembly according to claim 12, wherein the bridges of the attachment member and the flexible elongated member jointly define a cutting line.

14. The fixation assembly according to claim 13, wherein the cutting line extends substantially along the longitudinal axis of the attachment member.

15. The fixation assembly according to claim 11, wherein the attachment member incudes at least two bridges that are arranged parallel to each other.

16. The fixation assembly according to claim 10, wherein the first attachment section and the second attachment section are arranged on opposite lateral sides of the flexible elongated member.

17. The fixation assembly according to claim 10, wherein each of the first attachment section and the second attachment section has at least four openings for receiving a bone fastener.

18. The fixation assembly according to claim 10, wherein the first attachment section and the second attachment section are integrally formed with the flexible elongated member.

19. A fixation assembly for securing parts of a sternum, the assembly comprising:
    a flexible elongated member including a locking structure configured to secure the flexible elongated member in a loop around the sternum parts; and
    an attachment member coupled to the flexible elongated member, wherein the attachment member includes:
        a first attachment section comprising at least one opening for receiving a bone fastener;
        a second attachment section comprising at least one opening for receiving a bone fastener; and
        bridges configured to connect the first and second attachment section to each other and to be cut with a surgical tool, wherein the attachment member is cast in the flexible elongated member.

20. A fixation assembly for securing parts of a sternum, the assembly comprising:
- a flexible elongated member including a locking structure configured to secure the flexible elongated member in a loop around the sternum parts; and
- an attachment member having at least one opening for receiving a bone fastener, wherein the attachment member is coupled to the flexible elongated member, wherein the attachment member includes:
  - a first attachment section configured to be secured to the sternum;
  - a second attachment section configured to be secured to the sternum; and
  - multiple bridges configured to connect the first and second attachment section to each other and configured to be cut with a surgical tool;
- wherein the bridges of the attachment member and the flexible elongated member jointly define a cutting line, and
- wherein the attachment member is cast in the flexible elongated member.

* * * * *